(12) United States Patent
Bhate

(10) Patent No.: US 11,707,706 B1
(45) Date of Patent: Jul. 25, 2023

(54) CORONA DISINFECTING AIR FILTER SYSTEMS

(71) Applicant: Suresh Bhate, Niskayuna, NY (US)

(72) Inventor: Suresh Bhate, Niskayuna, NY (US)

(*) Notice: Subject to any disclaimer, the term of this patent is extended or adjusted under 35 U.S.C. 154(b) by 0 days.

(21) Appl. No.: 17/387,509

(22) Filed: Jul. 28, 2021

Related U.S. Application Data

(60) Provisional application No. 63/058,608, filed on Jul. 30, 2020.

(51) Int. Cl.
    B01D 46/00 (2022.01)
    B01D 39/12 (2006.01)
    (Continued)

(52) U.S. Cl.
    CPC .......... B01D 39/12 (2013.01); A41D 13/1192 (2013.01); A61L 9/20 (2013.01); A62B 23/02 (2013.01); B01D 46/0005 (2013.01); B01D 46/0028 (2013.01); B01D 46/62 (2022.01); F24F 8/10 (2021.01); F24F 8/22 (2021.01); *A61L 2209/12* (2013.01); *A61L 2209/14* (2013.01); *A61L 2209/15* (2013.01); *A61L 2209/16* (2013.01); *B01D 2239/0442* (2013.01); *B01D 2239/1208* (2013.01); *B01D 2275/10* (2013.01); *B01D 2279/50* (2013.01); *B01D 2279/65* (2013.01)

(58) Field of Classification Search
CPC ............ B01D 46/0005; B01D 46/0028; B01D 39/12; F24F 8/10; F24F 8/22
See application file for complete search history.

(56) References Cited

U.S. PATENT DOCUMENTS 10,905,790 B1 * 2/2021 Moore ..................... A61L 2/10
11,105,522 B2 * 8/2021 Kleinberger ............ F24F 3/167
(Continued)

OTHER PUBLICATIONS

EPA Press Release, EPA Registers Copper Surfaces for Residual Use Against Coronavirus, printout from the Internet on Jul. 22, 2021, https://www.epa.gov/newsreleases/epa-registers-copper-surfaces-residual-use-against-coronavirus, 4 pages, Feb. 10, 2021.
(Continued)

*Primary Examiner* — Robert A Hopkins
(74) *Attorney, Agent, or Firm* — Heslin Rothenberg Farley & Mesiti PC

(57) ABSTRACT

The present disclosure relates generally to air filtration devices. More specifically, but not exclusively, the present disclosure relates to an air filtration device comprised of a copper (or copper alloy) medium to inactivate airborne pathogens (e.g., viruses, bacteria, coronaviruses, COVID-19, etc.) and mitigate harmful exposure to said pathogens. The copper medium is a porous mesh (i.e., copper wool) that is positioned within or on a structure to provide support. The air filtration device may be positioned in an HVAC system such that an air stream flows through the copper medium to inactivate airborne pathogens, such as viruses, in the air stream. The air filtration device may be used in combination with, or in addition to, existing HVAC system conventional air filters (e.g., HEPA filters). The air filtration device includes a copper medium positioned on a face mask to inactivate airborne pathogens during respiratory processes.

38 Claims, 18 Drawing Sheets

(51) Int. Cl.
*F24F 8/10* (2021.01)
*F24F 8/22* (2021.01)
*A61L 9/20* (2006.01)
*A41D 13/11* (2006.01)
*A62B 23/02* (2006.01)
*B01D 46/62* (2022.01)

(56) References Cited

U.S. PATENT DOCUMENTS

2016/0015098 A1* 1/2016 Conlon .............. A41D 13/1192
 128/863
2021/0154610 A1* 5/2021 Carredo ................ B01D 39/12
2021/0396408 A1* 12/2021 Saieva ..................... B03C 3/47

OTHER PUBLICATIONS

DoctorsAirPurifier Revolutionary Air Purification, available from AIRDoctor, LLC, www.airdoctorpro.com, printout from the Internet on Jul. 22, 2021, https://web.archive.org/web/20180726085032/https://www.airdoctorpro.com/, (Wayback Verification Crawl Presence dated Jul. 26, 2018), 8 pages, Jul. 26, 2018.

M. Vincent et al. "Contact Killing and Antimicrobial Properties of Copper," Journal of Applied Microbiology, vol. 6 Issue 6, pp. 1032-1046, 2017.

Sarah L. Warnes et al. "Human Coronavirus 229E Remains Infectious on Common Touch Surface Materials," Centre for Biological Sciences, University of Southampton, Southampton, United Kingdom, vol. 6 Issue 6, e01697-15, 10 pages, Nov./Dec. 2015.

A. Gulati et al. "A Comprehensive Review of Manifestations of Novel Coronaviruses in the Context of Deadly COVID-19 Pandemic," The American Journal of the Medical Sciences, vol. 360, Issue 1, pp. 5-34, Jul. 2020.

SHYCOCAN—A Device to Disable Coronaviruses—to be Marketed Under US-FDA's Enforcement Discretion During the COVID-19 Public Health Emergency, Cision PR Newswire, printout from the Internet on Jul. 22, 2021, https://www.prnewswire.com/news-releases/shycocan—a-device-to-disable-coronaviruses—to-be-marketed-under-us-fdas-enforcement-discretion-during-the-covid-19-public-health-emergency-301098817.html?tc=eml_cleartime, 5 pages, Jul. 23, 2020.

* cited by examiner

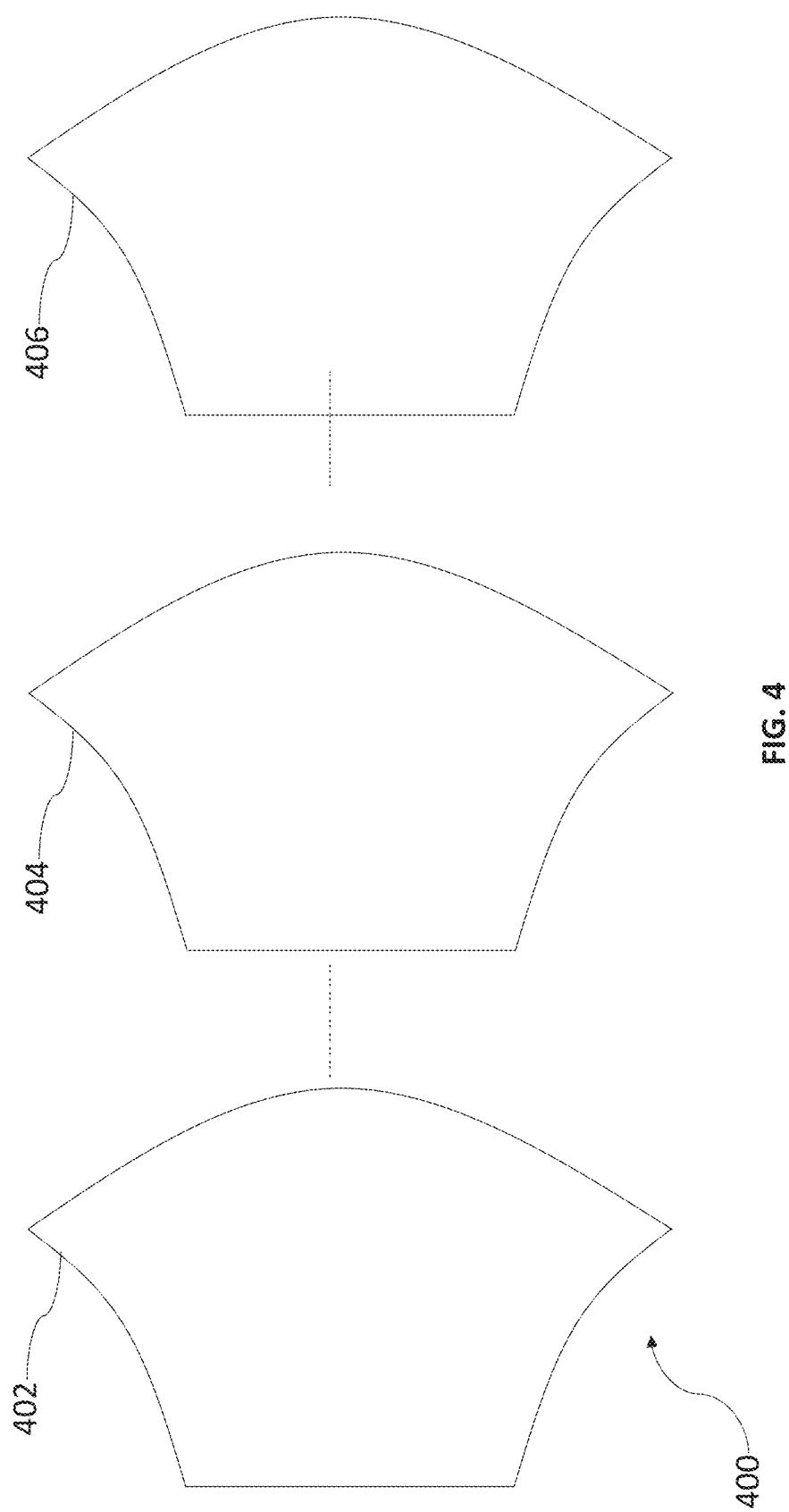

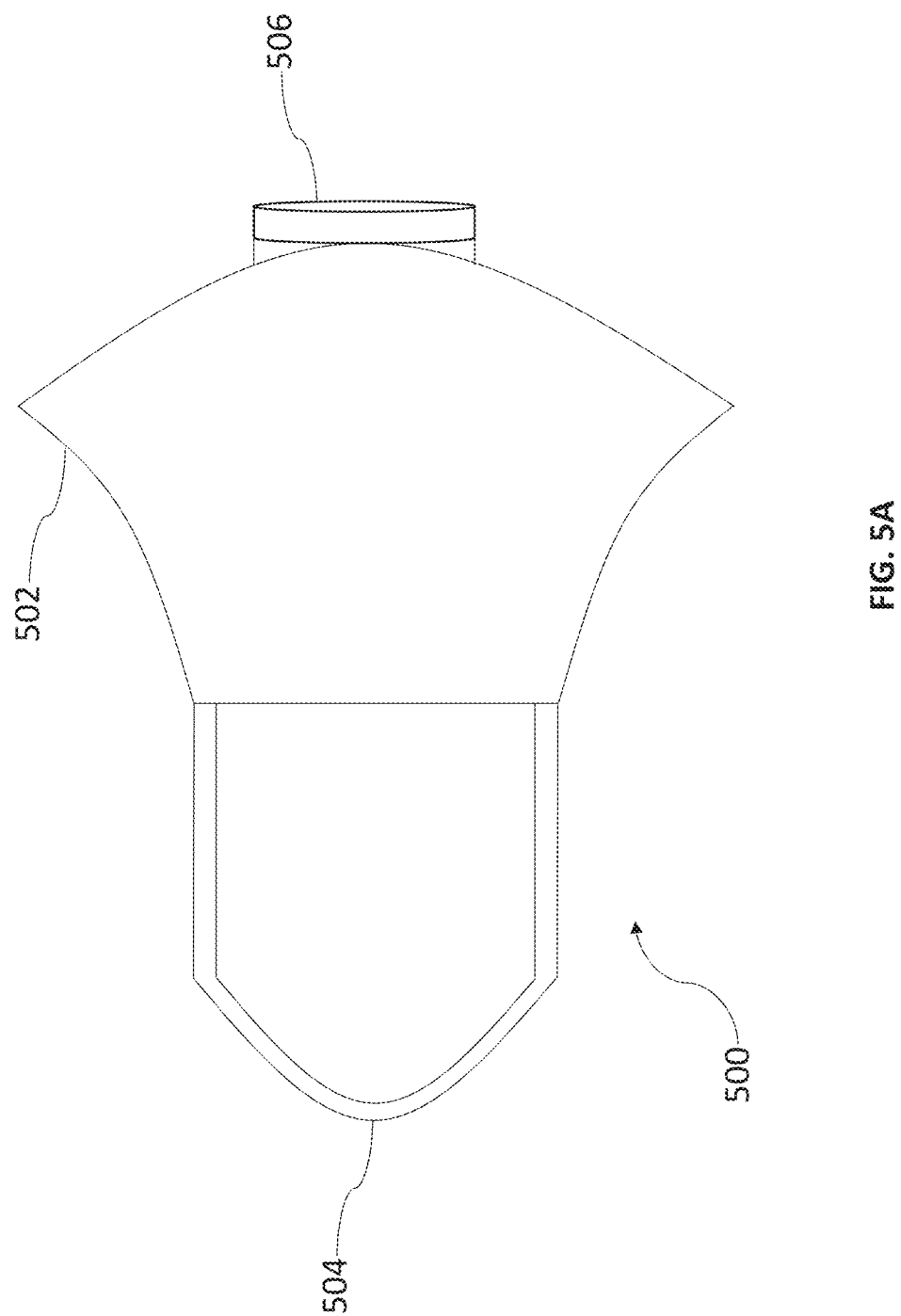

```
1300 ─┐
       ↘
   ┌─────────────────────────────────────────┐
   │ PROVIDING A COPPER WOOL MEDIUM          │
   │ CONFIGURED TO INACTIVATE VIRUSES FROM   │─ 1310
   │ AN AIR STREAM FLOWING THERETHROUGH      │
   └─────────────────────────────────────────┘
                      │
                      ▼
   ┌─────────────────────────────────────────┐
   │ ASSEMBLING AN ELONGATE SECTION ONTO EACH│─ 1320
   │ PERIMETER EDGE OF THE COPPER WOOL MEDIUM│
   └─────────────────────────────────────────┘
                      │
                      ▼
   ┌─────────────────────────────────────────┐
   │ JOINING THE ELONGATE SECTIONS BY WAY OF CORNER │─ 1330
   │ SECTIONS SECTION TO CREATE A RIGID FRAME       │
   └─────────────────────────────────────────┘
                      │
                      ▼
   ┌─────────────────────────────────────────┐
   │ POSITIONING THE COPPER WOOL             │─ 1340
   │ MEDIUM WITHIN A VENTILATION SYSTEM      │
   └─────────────────────────────────────────┘
                      │
                      ▼
   ┌─────────────────────────────────────────┐
   │ ADJUSTING THE RIGID FRAME TO DIRECT THE AIR STREAM │─ 1350
   │ TO FLOW THROUGH THE COPPER WOOL MEDIUM             │
   └─────────────────────────────────────────┘
```

FIG. 12

CORONA DISINFECTING AIR FILTER SYSTEMS

CLAIM TO PRIORITY

This application claims priority to U.S. Provisional Patent Application No. 63/058,608, filed Jul. 30, 2020, entitled "Corona Disinfecting Air Filter Systems", the disclosure of which is hereby incorporated by reference herein in its entirety.

TECHNICAL FIELD

The present disclosure relates generally to air filtration devices. More specifically, but not exclusively, the present disclosure relates to air filtration devices including or comprised of a copper, or copper alloy, medium to inactivate airborne pathogens (e.g., viruses, bacteria, coronaviruses, COVID-19, etc.) and mitigate harmful exposure to said pathogens.

BACKGROUND

The global pandemic caused by an infectious novel coronavirus 2019-nCoV (COVID-19) has been rapidly spreading since December 2019. As of April 2020, the outbreak has spread to over 210 countries, with over 2.4 million confirmed cases and over 170,000 deaths. COVID-19 is a respiratory pathogen where novel methods to mitigate transmission are required to deter the harmful effects of the pandemic. For a comprehensive review of COVID-19, see The American Journal of the Medical Sciences (Volume 360, Issue 1, ISSN 0002-9629)(2020), A Comprehensive Review of Manifestations of Novel Coronaviruses in the Context of Deadly COVID-19 Pandemic, A. Gulati, C. Pomeranz, Z. Qamar, S. Thomas, D. Frisch, G. George, R. Summer, J. DeSimone, B. Sundaram, available at http://www.sciencedirect.com/science/article/pii/S0002962920301798.

Copper is a metal element with atomic symbol Cu that occurs naturally throughout the environment. Copper has established antimicrobial properties that are effective against bacteria, fungi, and virus infections. Various studies have been conducted regarding the antimicrobial properties of copper. Research article Contact Killing and Antimicrobial Properties of Copper provides a comprehensive summary of copper as a metallic antimicrobial agent. See Journal of Applied Microbiology (ISSN 1364-5072), Contact Killing and Antimicrobial Properties of Copper (Sep. 17, 2017), M. Vincent, R. E. Duval, P. Hartemann, M. Engels-Deutsch.

Heating, ventilation, and air conditioning (HVAC) systems regulate indoor environments. HVAC systems, in pertinent part, maintain acceptable indoor air quality through ventilation. Ventilation is the process of exchanging air in any space to provide high quality air involving temperature and/or humidity control, oxygen replenishment, and the removal of harmful bacteria. HVAC systems are equipped with air filtering systems to provide a semblance of purified air to occupants indoors. HVAC systems incorporate one or more filters to remove particles from the air that passes through the filter. Typically, high-efficiency particulate air (HEPA) filters are employed in ventilation systems. HEPA filters are mechanical air filters, which are operable to remove airborne particles with a size of 0.3 microns ($\mu m$), and even smaller airborne particles such as 0.1 microns ($\mu m$) or lower, to purify air and mitigate the risk of indoor air contamination with particles. Most HEPA filters are about 5 inches thick. Many HEPA filters are not pleated. HEPA filters require periodic cleaning and/or replacement to function properly.

SUMMARY

The present disclosure is directed towards air filtration devices having or comprised of copper wool to inactivate airborne pathogens (e.g., viruses, bacteria, coronaviruses, COVID-19, etc.) and mitigate harmful exposure to airborne pathogens. As used herein, the term copper wool or copper wool material includes, but not limited to, one or more copper screens of any mesh size, copper coated filter papers, copper coated foam, copper foam, a bundle of copper filaments, copper coated cloths, copper or copper coated any other material (such as steel, aluminum, etc.) screens or structures. Copper coating can be by electroless or electroplating, flame spraying, chemical vapor deposition (CVD), sputtering, vacuum deposition or evaporation coating. The term copper also includes all copper alloys listed in Table 1 herein, which are recognized by EPA (Environmental Protection Agency of U.S. Government) as having antimicrobial properties.

In one aspect, the present disclosure is directed to an air filter to inactivate airborne pathogens (e.g., viruses, bacteria, coronaviruses, COVID-19, etc.) in an air stream flowing therethrough. The air filter includes a copper wool medium configured to inactivate pathogens from the air stream flowing therethrough. The copper wool medium is porous and includes or comprised of one or more copper or copper alloys with antimicrobial properties. A frame including or comprised of a rigid or semi-rigid material is configured to support and direct the air stream through the copper wool medium. The frame may be configured to be adjusted to accommodate an interior of a ventilation system.

In a second aspect, the present disclosure is directed to an air filter to inactivate airborne pathogens (e.g., viruses, bacteria, coronaviruses, COVID-19, etc.) in an air stream flowing therethrough. The air filter includes a filter medium configured to remove and inactivate contaminants from the air stream flowing therethrough. The filter medium further includes a first filter layer, a second filter layer, and a frame configured to direct the air stream therethrough. The first filter layer is a conventional air filter, such as a high-efficiency particulate air (HEPA) filter. The second filter layer includes or is comprised of a copper wool medium. The copper wool medium is porous and includes or is comprised of one or more copper or copper alloys with antimicrobial properties. The first filter layer is positioned upstream of the air stream flowing therethrough relative to the position of the second filter layer. The frame may be configured to be adjusted to accommodate an interior of a ventilation system.

In a third aspect, the present disclosure is directed to a face mask to inactivate airborne pathogens (e.g., viruses, bacteria, coronaviruses, COVID-19, etc.) in an air stream flowing therethrough to mitigate the risk of pathogen transmission. The face mask includes a textile medium and a copper wool medium. The textile medium and the copper wool medium include or is comprised of dimensions that are substantially similar to the bottom portion of a human face. The textile medium and the copper wool medium are configured to inactivate airborne pathogens from a respiratory air stream.

In a fourth aspect, the present disclosure is directed to a method mask to remove or deteriorate and/or inactivate airborne pathogens (e.g., viruses, bacteria, coronaviruses, COVID-19, etc.) in an air stream flowing therethrough. The method includes providing a copper wool medium configured to inactivate pathogens from an air stream flowing therethrough; assembling an elongate section onto each perimeter edge of the copper wool medium; joining the elongate sections by way of corner sections section to create a rigid frame; positioning the copper wool medium within a ventilation system; and adjusting the rigid frame to cause the air stream to flow through the copper wool medium. Providing the copper wool medium includes selecting one or more copper or copper alloys that possess antimicrobial properties. Providing the copper wool medium includes selecting a porosity that is preferably less than or equal to 3 μm. Positioning the copper wool medium includes orienting the copper wool medium such that the copper wool medium is downstream of a filter medium.

In a fifth aspect, the present disclosure is directed to an air filtration system to inactivate airborne pathogens (e.g., viruses, bacteria, coronaviruses, COVID-19, etc.) in an air stream flowing therethrough. The air filtration system includes first filter, a second filter, and a channel extending between the first filter and the second filter such that the first filter and the second filter are in fluid communication. The first filter further includes a filter medium configured to remove or deteriorate contaminants from an air stream flowing through a ventilation system. A first frame is configured to direct the air stream through the filter medium. The second filter further includes a copper wool medium configured to inactivate pathogens from an air stream flowing therethrough. A second frame is configured to direct the air stream through the copper wool medium. The channel further includes a channel frame, a first ultraviolet light source affixed to an interior surface of the channel frame, and a power source. The first filter is affixed to a first end of the channel frame and the second filter is affixed to a second end of the channel frame, wherein the first end is positioned opposite the second end. The first filter is positioned upstream of the air stream flowing through the ventilation system relative to the position of the second filter layer. The copper wool medium includes or is comprised of one or more copper or copper alloys with antimicrobial properties. The copper wool medium preferably includes or is comprised of a porosity less than or equal to 3 μm.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 4 depicts an exploded side view of a face mask device having or comprised of copper wool, according to an embodiment of the present disclosure.

FIG. 5A depicts a side view of a face mask device having or comprised of copper wool, according to an embodiment of the present disclosure.

FIG. 12 is a flowchart of a method for removing or deteriorating airborne contaminants from air, according to an embodiment of the present disclosure.

DETAILED DESCRIPTION

Figure 1:
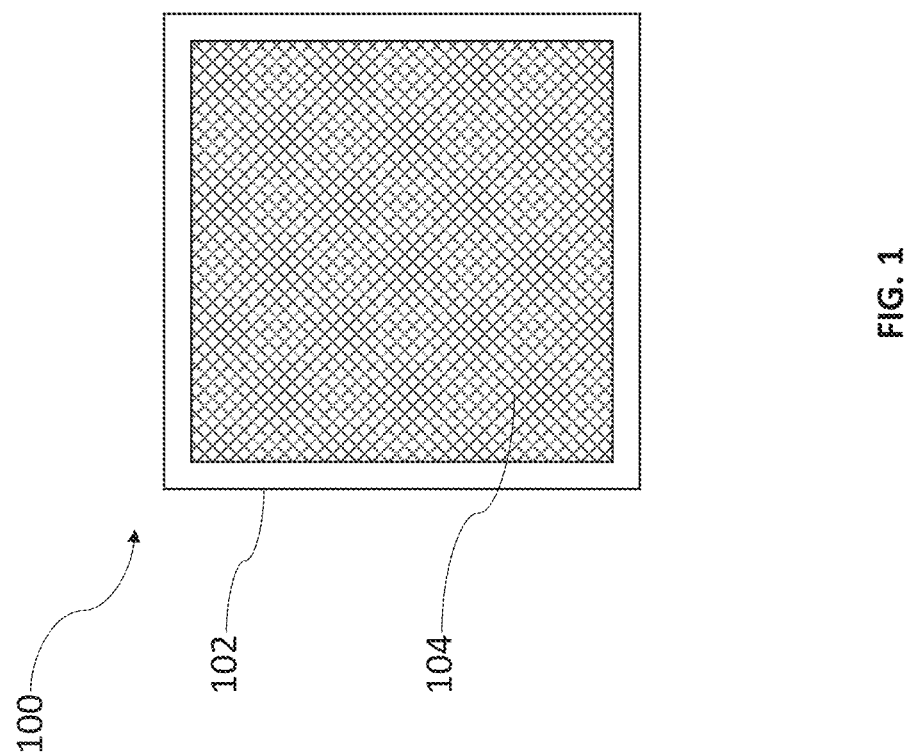
FIG. 1 depicts a front view of a copper wool air filter, according to an embodiment of the present disclosure.

Generally stated, the present disclosure is directed to air filtration devices having or comprised of copper wool. The antimicrobial properties of copper and the unique structural conformation of copper wool may be useful to inactivate airborne pathogens (e.g., viruses, bacteria, coronaviruses, COVID-19, etc.) in an air stream flowing through the air filtration devices to mitigate the risk of harmful exposure to airborne pathogens (e.g., mitigate the risk of COVID-19 transmission). An air filtration device includes, but is not limited to, air filters for ventilation systems and face masks. The present disclosure is applicable in homes, hotels and motel rooms, small restaurants/bars, stores, small business facilities, workplaces, and other residential, commercial, and business locations, etc. As used herein, the term copper wool or copper wool material includes, but is not limited to, one or more copper screens of any mesh size, copper coated filter papers, copper coated foam, copper foam, a bundle of copper filaments, copper coated cloths, copper or copper coated any other material (such as steel, aluminum, etc.)

screens or structures. Copper coating can be by electroless or electroplating, flame spraying, chemical vapor deposition (CVD), sputtering, vacuum deposition or evaporation coating. The term copper also includes all copper alloys listed in Table 1 herein, which are recognized by EPA (Environmental Protection Agency of U.S. Government) as having antimicrobial properties.

Embodiments of the present disclosure may include or be comprised of material that may "inactivate" pathogens such as viruses. Pathogen inactivation selectively damages genetic material that prevents the pathogen (e.g., viruses, bacteria, and parasites) from transmitting infection, often due to an inability to replicate DNA and/or RNA. The inactivation of viruses may occur through the interaction of metallic ions (e.g., $Cu^+$ and $Cu^{2+}$) that bond with a virus. For example, an air stream having or comprised of COVID-19 particles is directed through a porous copper wool medium. COVID-19 particles encounter the porous copper wool medium and, thus, encounter metallic ions in the vicinity. The interaction between the porous copper wool medium and COVID-19 particles results in an inactive state of COVID-19, wherein the inactive state of COVID-19 is unable to replicate in an organism that is unaffected by COVID-19.

Embodiments of the present disclosure include or are comprised of copper or copper alloy products with antimicrobial properties useful to inactivate pathogens (e.g., viruses, bacteria, coronaviruses, COVID-19, etc.). Table 1 provides a list of the Unified Number System (UNS) designations for 510 copper and copper alloy products registered with Environmental Protection Agency (EPA) determined to have antimicrobial properties. The UNS is the accepted alloy designation system in North America for wrought and cast copper and copper alloy products. Embodiments of the present disclosure may include one or more of the identified copper or copper alloy products referenced in Table 1. The copper and copper alloys identified in Table 1 may hereinafter be collectively referred to as "Copper Material" (i.e., the term "Copper Material" refers to one or more of the identified coppers and copper alloys identified in Table 1).

TABLE 1

EPA Registered Antimicrobial Copper Alloys (UNS Numbers)

|  | A | B | C | D | E | F | G | H |
|---|---|---|---|---|---|---|---|---|
| 1 | C10100 | C14750 | C19260 | C43000 | C61200 | C66430 | C71600 | C87800 |
| 2 | C10200 | C15000 | C19280 | C43400 | C61300 | C66500 | C71630 | C87845 |
| 3 | C10300 | C15100 | C19300 | C43500 | C61400 | C66700 | C71640 | C87850 |
| 4 | C10400 | C15150 | C19400 | C43600 | C61500 | C66850 | C71700 | C87860 |
| 5 | C10500 | C15500 | C19410 | C43800 | C61550 | C66900 | C72500 | C87870 |
| 6 | C10700 | C15600 | C19419 | C44200 | C61600 | C66908 | C72600 | C89320 |
| 7 | C10800 | C15650 | C19450 | C44250 | C61700 | C66910 | C72650 | C89510 |
| 8 | C10900 | C15710 | C19500 | C44300 | C61800 | C66913 | C72660 | C89520 |
| 9 | C10910 | C15715 | C19600 | C44400 | C61810 | C66915 | C72700 | C89537 |
| 10 | C10920 | C15720 | C19700 | C44500 | C61900 | C66920 | C72800 | C89550 |
| 11 | C10930 | C15725 | C19710 | C44750 | C62000 | C66925 | C72900 | C89560 |
| 12 | C10940 | C15730 | C19720 | C45450 | C62200 | C66930 | C72950 | C89570 |
| 13 | C11000 | C15735 | C19750 | C45470 | C62300 | C66950 | C73100 | C89580 |
| 14 | C11010 | C15750 | C19800 | C46210 | C62400 | C68300 | C73200 | C89720 |
| 15 | C11020 | C15760 | C19810 | C46250 | C62500 | C68350 | C73500 | C89833 |
| 16 | C11025 | C15780 | C19900 | C49250 | C62580 | C68400 | C73800 | C89835 |
| 17 | C11030 | C15790 | C19910 | C49260 | C62581 | C68410 | C74000 | C89842 |
| 18 | C11040 | C15815 | C20500 | C49300 | C62582 | C68700 | C74300 | C89845 |
| 19 | C11045 | C15900 | C21000 | C49340 | C62600 | C68800 | C74400 | C89940 |
| 20 | C11100 | C16200 | C22000 | C49350 | C62730 | C68900 | C74500 | C90280 |
| 21 | C11300 | C16210 | C22600 | C49355 | C62800 | C69000 | C75200 | C90400 |
| 22 | C11400 | C16400 | C23000 | C49360 | C63000 | C69050 | C75700 | C90410 |
| 23 | C11500 | C16500 | C23030 | C50100 | C63010 | C69100 | C75720 | C90420 |
| 24 | C11600 | C17000 | C23400 | C50150 | C63020 | C69150 | C76400 | C90430 |
| 25 | C11700 | C17200 | C24000 | C50200 | C63200 | C69200 | C80100 | C94700 |
| 26 | C11900 | C17400 | C25000 | C50500 | C63230 | C69220 | C80300 | C95200 |
| 27 | C11904 | C17410 | C25600 | C50510 | C63280 | C69230 | C80410 | C95210 |
| 28 | C11905 | C17420 | C26000 | C50580 | C63300 | C69250 | C80500 | C95220 |
| 29 | C11907 | C17450 | C26100 | C50590 | C63380 | C69300 | C80700 | C95300 |
| 30 | C12000 | C17460 | C26130 | C50700 | C63400 | C69310 | C80900 | C95400 |
| 31 | C12100 | C17500 | C26200 | C50705 | C63700 | C70100 | C81100 | C95410 |
| 32 | C12200 | C17510 | C26800 | C50710 | C63800 | C70200 | C81200 | C95420 |
| 33 | C12210 | C17520 | C27000 | C50715 | C63900 | C70230 | C81300 | C95430 |
| 34 | C12220 | C17530 | C27200 | C50725 | C64200 | C70240 | C81700 | C95500 |
| 35 | C12300 | C17600 | C27400 | C50780 | C64210 | C70250 | C81800 | C95510 |
| 36 | C12500 | C17700 | C28000 | C50800 | C64250 | C70252 | C82000 | C95520 |
| 37 | C12510 | C18620 | C28300 | C50900 | C64400 | C70260 | C82100 | C95600 |
| 38 | C12700 | C18625 | C28310 | C51000 | C64700 | C70265 | C82200 | C95700 |
| 39 | C12800 | C18660 | C28320 | C51080 | C64710 | C70270 | C82400 | C95710 |
| 40 | C12900 | C18661 | C28330 | C51100 | C64720 | C70275 | C82500 | C95720 |
| 41 | C13100 | C18665 | C40400 | C51180 | C64725 | C70280 | C82510 | C95800 |
| 42 | C13150 | C18835 | C40410 | C51190 | C64727 | C70290 | C82600 | C95810 |
| 43 | C13400 | C18900 | C40500 | C51800 | C64728 | C70300 | C82700 | C95820 |
| 44 | C13500 | C18910 | C40800 | C51900 | C64730 | C70310 | C82800 | C95900 |
| 45 | C13600 | C18980 | C40810 | C51980 | C64740 | C70350 | C83460 | C96200 |
| 46 | C13700 | C19000 | C40820 | C52100 | C64745 | C70370 | C83470 | C96300 |
| 47 | C14180 | C19002 | C40850 | C52180 | C64750 | C70400 | C84000 | C96400 |
| 48 | C14181 | C19010 | C40860 | C52400 | C64760 | C70500 | C84010 | C96600 |
| 49 | C14200 | C19015 | C40950 | C52480 | C64770 | C70600 | C84020 | C96700 |

TABLE 1-continued

EPA Registered Antimicrobial Copper Alloys (UNS Numbers)

| | A | B | C | D | E | F | G | H |
|---|---|---|---|---|---|---|---|---|
| 50 | C14210 | C19020 | C41000 | C52600 | C64780 | C70610 | C84030 | C96800 |
| 51 | C14300 | C19022 | C41100 | C52900 | C64785 | C70620 | C85450 | C96900 |
| 52 | C14310 | C19024 | C41110 | C55180 | C64800 | C70690 | C85470 | C96950 |
| 53 | C14400 | C19025 | C41120 | C55181 | C64900 | C70700 | C85550 | C96970 |
| 54 | C14410 | C19027 | C41125 | C55280 | C65100 | C70800 | C85900 | C99300 |
| 55 | C14415 | C19030 | C41300 | C55281 | C65300 | C70900 | C85910 | C99400 |
| 56 | C14420 | C19040 | C41500 | C55282 | C65500 | C71000 | C85920 | C99500 |
| 57 | C14430 | C19050 | C42000 | C55283 | C65600 | C71100 | C85930 | C99710 |
| 58 | C14440 | C19170 | C42100 | C55284 | C65620 | C71110 | C86350 | C99760 |
| 59 | C14500 | C19200 | C42200 | C55285 | C65800 | C71300 | C87300 | C99761 |
| 60 | C14510 | C19210 | C42210 | C55385 | C66200 | C71500 | C87500 | C99770 |
| 61 | C14520 | C19215 | C42220 | C55386 | C66300 | C71520 | C87600 | C99771 |
| 62 | C14530 | C19220 | C42500 | C60600 | C66400 | C71580 | C87610 | C99780 |
| 63 | C14700 | C19240 | C42520 | C60700 | C66410 | C71581 | C87700 | |
| 64 | C14710 | C19250 | C42600 | C61000 | C66420 | C71590 | C87710 | |

Embodiments of the present disclosure pertaining to an air filter to inactivate airborne pathogens (e.g., viruses, bacteria, coronaviruses, COVID-19, etc.) in an air stream flowing therethrough may include or be comprised of one or more of the following: (i) one or more copper wool layers having or comprised of Copper Material; (ii) one or more mesh layers having or comprised of Copper Material; (iii) two or more layers, where at least one layer having or is comprised of Copper Material; (iv) Copper Material nanoparticles; (v) textile fibers having or comprised of Copper Material; (vi) textile fibers having or comprised of Copper Material nanoparticles; (vii) a copper wool layer with a porosity less than 10μ; (viii) a copper wool layer with a porosity greater than 0.125μ; (ix) Copper Material powder; (x) a copper wool medium with antimicrobial properties, and (xi) other metals which may have higher resistance to develop a surface coating due to exposure to atmospheric conditions.

In some embodiments, a face mask device to inactivate airborne pathogens (e.g., viruses, bacteria, coronaviruses, COVID-19, etc.) in air stream flowing therethrough includes or is comprised of one or more of the following: (i) one or more copper wool layers having or comprised of Copper Material; (ii) a copper wool layer having or comprised of Copper Material positioned between two or more textile layers; (iii) a copper wool layer having or comprised of Copper Material positioned on an outer surface of the face mask device; (iv) a copper wool layer having or comprised of Copper Material positioned on an inner surface of the face mask device; (v) a detachable copper wool layer having or comprised of Copper Material; (vi) Copper Material nanoparticles; (vii) a copper wool layer with a porosity less than 1μ; (viii) a copper wool layer with a porosity greater than 0.125μ; (ix) Copper Material powder; (x) textiles having or comprised of Copper Material; (xi) textile having or comprised of Copper Material nanoparticles; and (xii) a copper wool medium with antimicrobial properties.

In some embodiments, the present disclosure includes or is comprised of a "conventional air filter." A "conventional air filter," refers to a filtration device or material that is used in existing ventilation system to remove particles from air streams to increase the quality of the air. Conventional air filters may include, but is not limited to, one or more of the following: (i) high-efficiency particulate air (HEPA) filters; (ii) fiberglass filters; (iii) pleated air filters; and (iv) any other material, or combination of material, that is presently utilized to purify an air stream flowing therethrough.

In some embodiments, an air filter to inactivate airborne pathogens (e.g., viruses, bacteria, coronaviruses, COVID-19, etc.) in an air stream flowing therethrough includes or is comprised of at least a first layer and a second layer, wherein the first layer is a conventional air filter which removes or traps particles based upon size, such as a HEPA filter, and the second layer is copper wool including or comprised of Copper Material which functions to inactivate airborne pathogens. The first layer and second layer may be held together by a frame. The frame may include or be comprised of Copper Material. The filter may be positioned within a HVAC system such that the second layer is downstream of the first layer.

Alternatively, the first layer (i.e., HEPA filter) and the second layer (i.e., copper wool) are stacked and held together by a chemical adhesive. For example, a polyurethane adhesive is applied to the perimeter of the HEPA filter and the copper wool is subsequently applied to bond the two layers.

In some embodiments, an air filter includes or is comprised of at least one copper wool medium with a first porosity. The at least one copper wool medium may be configured such that a flowing air stream directed through the at least one copper wool medium substantially flows therethrough without a significant change in pressure. The at least one copper wool medium may be configured such that the first porosity enables pathogens (such as coronaviruses) within the flowing air stream to contact, or be in the proximity of, the at least one copper wool medium. The first porosity may range from 0.125 μm to 10 μm.

For example, an air filter may include or comprised of a copper wool medium with a porosity that is slightly greater than 0.125 μm. COVID-19 particles are approximately 0.125 μm. An air stream includes or comprised of COVID-19 particles is directed through the copper wool medium. The COVID-19 particles directly contact, or come within the proximity of, the copper wool medium. The copper wool medium—due to antimicrobial properties—inactivates the COVID-19. As such, individuals that breath in air that has passed through the copper wool medium will not result in COVID-19 transmission because the virus particles are inactive.

Alternatively, an air filter includes or comprised of at least one copper wool medium with a first porosity, wherein the first porosity is 3 μm. An air stream is directed through the at least one copper wool medium with the first porosity. Any pathogen particles within the air stream (i.e., COVID-19 virus particles) are inactivated upon passing through the copper wool medium.

In some embodiments, an air filter to inactivate airborne pathogens (e.g., viruses, bacteria, coronaviruses, COVID-19, etc.) in an air stream flowing therethrough includes or comprised of two or more copper wool layers, wherein the two or more copper wool layers includes or are comprised of Copper Material. The two or more copper wool layers may have different porosity values. The two or more copper wool layers are stacked adjacent to each other and held together by a mechanical device. For example, four elongate sides of a square frame are positioned on the perimeter of two copper wool layers stacked together. Four corners hold the elongate sides together to provide a rigid structure for the filter to be placed in a ventilation system.

Alternatively, two or more copper wool layers may be aligned and held together by chemical means. For example, a first copper wool layer and a second copper wool layer of equivalent surface area are positioned adjacent to each other. An external heat source melts the perimeter of the first and second copper wool layers to bond the layers together.

In some embodiments, an air filter device to inactivate airborne pathogens (e.g., viruses, bacteria, coronaviruses, COVID-19, etc.) in an air stream flowing therethrough includes or is comprised of three layers. A first layer includes or is comprised of copper wool with a first porosity; a second layer includes or is comprised of a textile embedded with Copper Material nanoparticles; and a third layer includes or is comprised of copper wool with a second porosity. The three layers are aligned and stacked together such that the second layer is positioned between the first and third layer. The three layers are held together by mechanical or chemical forces (e.g., a frame, adhesive compound, etc.).

In some embodiments, an air filter device to inactivate airborne pathogens (e.g., viruses, bacteria, coronaviruses, COVID-19, etc.) includes or is comprised of a first layer of copper wool with a first porosity. A second layer includes or is comprised of Copper Material nanoparticles deposited on at least one surface of the first layer of copper wool. The first layer of copper wool may include or be comprised of the same Copper Material as the second layer of Copper Material nanoparticles. Deposition of Copper Material nanoparticles may occur through any chemical processes. Alternatively, a first layer of copper wool includes or is comprised of a first copper composition and a second layer of nanoparticles includes or is comprised of a second copper composition deposited on the first layer of copper wool.

In some embodiments, an air filter device to inactivate airborne pathogens (e.g., viruses, bacteria, coronaviruses, COVID-19, etc.) includes or is comprised of a copper wool medium with a first density. The first density is approximately 5% to 10% relative to a device having or is comprised of pure copper with substantially similar dimensions. For example, a filter includes or comprised of solid copper with dimensions of 24 inches×24 inches×⅛ inches (L×W×H) will weigh approximately 23.76 lbs. An air filter of the present disclosure includes or is comprised of copper wool with dimensions of 24 inches×24 inches×⅛ inches (L×W×H) will weigh approximately 1.188 lbs. to 2.376 lbs. (i.e., 5% to 10% relative to a device of substantially similar dimensions having or comprised of pure copper).

Alternatively, or additionally, an air filter device to inactivate airborne pathogens (e.g., viruses, bacteria, coronaviruses, COVID-19, etc.) includes or is comprised of at least a first copper wool medium with a first density and a second copper wool medium with a second density. The first density is approximately 5% to 10% relative to a device having or comprised of pure copper with substantially similar dimensions. The second density is approximately 5% to 10% relative to a device having or comprised of pure copper with substantially similar dimensions. For example, a filter comprised of solid copper with dimensions of 24 inches×24 inches×⅛ inches (L×W×H) will weigh approximately 23.76 lbs. An air filter of the present disclosure includes or is comprised of a first copper wool medium with dimensions of 24 inches×24 inches×⅛ inches (L×W×H) that weighs approximately 1.188 lbs. (i.e., 5% relative to a device of substantially similar dimensions having or comprised of pure copper). The air filter may further include or be comprised of a second copper wool medium with dimensions of 24 inches×24 inches×⅛ inches (L×W×H) will weigh approximately 2.376 lbs. (i.e., 10% relative to a device of substantially similar dimensions having or comprised of pure copper). The air filter is configured to direct an air stream through the first copper wool medium and second copper wool medium.

In some embodiments, an air filter device to inactivate airborne pathogens (e.g., viruses, bacteria, coronaviruses, COVID-19, etc.) includes or comprised of a copper wool medium is configured to obstruct the air stream flowing therethrough such that a majority of air particles within the air stream contact the copper wool medium. The air filter device is configured to obstruct an air stream flowing therethrough without a significant change in pressure drop (i.e., the degree of obstruction that the air filter device imparts on the air stream flowing therethrough does result in a significant increase in pressure drop or require a change in a circulation system where the air filter device is positioned). For example, an air filter device having or comprised of copper wool is positioned in a ventilation system and an air stream is directed therethrough. The air stream includes or is comprised of a plurality of air particles (e.g., oxygen, coronaviruses, COVID-19 particles, etc.). Most of the air particles, of the plurality of air particles, come into direct contact with copper wool when passing through the air filter device. The air filter device is configured to enable the flow of the air stream therethrough without a significant drop in pressure. As such, the use of the air filter device does not require a change in the operation of air circulation blowers or other equipment used to direct the air stream.

In some embodiments, an air filter device to inactivate airborne pathogens (e.g., viruses, bacteria, coronaviruses, COVID-19, etc.) having or comprised of a copper wool medium is positioned in a dehumidifier. The dehumidifier is configured to direct an air stream through the copper wool medium of the air filter device to inactivate airborne pathogens. The dehumidifier may be configured to direct an incoming air stream, an outgoing air stream, or both, through the copper wool medium. For example, an air filter device having or comprised of a copper wool medium is positioned in a dehumidifier device. The dehumidifier device is configured to direct an incoming air stream through the copper wool medium of the air filter device to inactivate airborne pathogens.

Alternatively, an air filter device to inactivate airborne pathogens (e.g., viruses, bacteria, coronaviruses, COVID-19, etc.) having or comprised of a copper wool medium is positioned in an air humidifier. The air humidifier is configured to direct an air stream through the copper wool medium of the air filter device to inactivate airborne pathogens. The air humidifier may be configured to direct an incoming air stream, an outgoing air stream, or both, through the copper wool medium. For example, an air filter device having or comprised of a copper wool medium is positioned in an air humidifier device. The air humidifier device is configured to direct an incoming air stream through the copper wool medium of the air filter device to inactivate airborne pathogens.

As a further alternative embodiment, an air filter device to inactivate airborne pathogens (e.g., viruses, bacteria, coronaviruses, COVID-19, etc.) having or comprised of a copper wool medium is positioned in an air purifier. The air purifier is configured to direct an air stream through the copper wool medium of the air filter device to inactivate airborne pathogens. The air purifier may be configured to direct an incoming air stream, an outgoing air stream, or both, through a copper wool medium. The air purifier may further include an ultraviolet light source configured to direct ultraviolet light to an incoming air stream, outgoing air stream, or both (see FIG. 7). For example, an air filter device includes or comprised of a copper wool medium is positioned in an air purifier device. The air purifier device is configured to direct an incoming air stream through the copper wool medium of the air filter device to inactivate airborne pathogens.

In some embodiments, an air filter device to inactivate airborne pathogens (e.g., viruses, bacteria, coronaviruses, COVID-19, etc.) includes or comprised of a copper wool medium is positioned in, or on, an air-drying device. The air-drying device directs a hot air stream to remove moisture from a surface (e.g., a bathroom hand dryer, a hair dryer). The air filter device is configured to direct the hot air stream from the air-drying device through the copper wool medium to inactivate airborne pathogens. For example, a hand dryer located in a bathroom directs a stream of hot air to remove excess water from a user's hands after washing. An air filter device having or comprised of a copper wool medium is positioned in the hand dryer such that the hand dryer is configured to direct the hot air stream through the copper wool medium to inactivate airborne pathogens (e.g., coronavirus particles).

As a further alternative embodiment, an air filter device to inactivate airborne pathogens (e.g., viruses, bacteria, coronaviruses, COVID-19, etc.) includes or comprised of a copper wool medium is affixed to a surface of an air-drying device. The air filter device is affixed to the surface of the air-drying device through mechanical means. The air filter device is affixed to a surface of the air-drying device such that a hot air stream is directed through the copper wool medium to inactivate airborne pathogens. For example, a hand dryer located in a bathroom directs a stream of hot air to remove excess water from a user's hands after washing through an aperture positioned on a surface of the hand dryer. An air filter device having or comprised of a copper wool medium is affixed to the surface of the hand dryer such that the hand dryer directs a hot air stream through the aperture positioned on the surface of the hand dryer and through the copper wool medium to inactivate airborne pathogens. In another embodiment, the incoming cold air is passed through the filter consisting of copper wool medium.

In some embodiments, a filter includes or is comprised of at least one layer and at least one ultraviolet (UV) light source. The at least one layer is a copper medium to inactivate airborne pathogens (e.g., viruses, bacteria, coronaviruses, COVID-19, etc.) in an air stream flowing therethrough. The at least one UV light source may be positioned such that UV light is transmitted to at least a portion of the at least one layer. Alternatively, a plurality of UV light sources may be used to transmit UV light across both surfaces of the at least one layer.

In some embodiments, at least one UV light source is positioned between a first filter layer and a second filter layer. The first filter layer may be a conventional air filter such as a high-efficiency particulate air (HEPA) filter. The second filter layer is a copper medium having or comprised of Copper Material (e.g., a copper wool layer). The at least one UV light source transmits ultraviolet rays to at least one surface of the first filter layer and at least one surface of the second filter layer. Alternatively, a plurality of UV light sources are positioned such that ultraviolet rays are transmitted to both surfaces of the first layer and the second layer.

In some embodiments, a device to inactivate airborne pathogens (e.g., viruses, bacteria, coronaviruses, COVID-19, etc.) flowing therethrough having or comprised of one or more of the following: (i) a conventional air filter; (ii) two or more conventional air filters; (iii) copper mesh; (iv) copper wool; (v) a textile having or comprised of copper alloy nanoparticles; (vi) a chamber having or comprised of one or more UV light sources; (vii) a chamber having or comprised of one or more UV light sources, wherein a first filter is affixed to a first end of the chamber and a second filter is affixed to a second end of the chamber; (viii) a chamber with an interior translucent surface having or is comprised of Copper Material nanoparticles; and (ix) a power source.

For example, a filtration device includes or is comprised of a chamber, wherein the chamber further includes or is comprised of a translucent material enclosing a plurality of UV light sources. The translucent material includes or is comprised of copper oxide nanoparticles. In the present embodiment, the chamber is a rectangle with a hollow channel along the center with two openings at opposite ends of the hollow channel. The first end has a mechanism to affix a HEPA filter to cover the first opening at the first end. The second end has a mechanism to affix a copper wool filter to cover the second opening at the second end. The filtration device is positioned in a ventilation system such that the second end (i.e., the copper wool filter) is downstream relative to the first end (i.e., the HEPA filter). Air flow passes through the HEPA filter through the chamber of UV light and through the copper wool filter. The plurality of UV light sources continuously disperses UV light into the chamber.

Alternatively, a plurality of UV light sources positioned along a chamber that enables fluid communication between a first filter and a second filter may be operable to disperse light at predetermined intervals. The intervals may be controlled by one or more computer implemented methods that programmatically determines intervals to direct power to the plurality of UV light sources through a circuit. For example, a plurality of UV light sources is positioned on a circuit that is controlled by computer logic. The computer logic transmits power to the UV light source for a ten second interval (i.e., turns the UV light source on), and subsequently prevents the transmission of power to the UV light source for a ten second interval (i.e., turns the UV light source off). The computer logic alternates between on and off states every ten seconds.

In some embodiments, a device to inactivate airborne pathogens (e.g., viruses, bacteria, coronaviruses, COVID-19, etc.) includes or is comprised of a chamber positioned between a first filter and a second filter. The first filter is a standard HVAC filter (e.g., HEPA filter, pleated filter, fiberglass filter, etc.). The second filter is a copper medium having or comprised of Copper Material. The second filter is positioned downstream—relative to the first filter—when used in an air filtration system. In the present embodiment, the first filter and the second filter are rectangles of equal dimensions; alternative structural configurations may be useful to accommodate HVAC infrastructure. The chamber is a rectangle where two faces opposite each other have dimensions that are identical, or substantially similar, to the dimensions of the first filter and second filter. The first filter is affixed to one face of the chamber, and the second filter is affixed to an opposite face of the chamber. The chamber further includes or is comprised of an airflow channel that extends through a substantial portion of the chamber's volume such that the first filter and second filter are in fluid communication with each other when each is affixed to the chamber. The four faces that enclose the airflow channel are four ultraviolet (UV) panels. Each UV panel includes or is comprised of three layers. An outer layer includes or is comprised of a durable material to maintain a rigid structure. A middle layer includes or is comprised of at least one UV light source; a plurality of UV light sources may also be useful. An inner layer includes or is comprised of a material that UV light can pass through. Other UV panel configurations that include two or more layers may also be useful.

In some embodiments, a middle layer of a UV panel further includes or is comprised of a panel circuit that connects at least one UV light source to an external power source. Alternatively, a UV panel is connected to an internal power source (e.g., a battery). The battery may be charged by existing infrastructure in the system through a physical connection or wireless energy transfer mechanisms.

In some embodiments, an inner layer of a UV panel includes or is comprised of Copper Material. The Copper Material may be embedded within a substrate (e.g., silicon, a polymer, etc.) by deposition methods.

In some embodiments, a method to inactivate airborne pathogens (e.g., viruses, bacteria, coronaviruses, COVID-19, etc.) in an air stream flowing through an air passageway includes or is comprised of the following steps: (a) passing airflow through a first filter, wherein the first filter is a conventional air filter; (b) directing air flow through a chamber, wherein the chamber extends between the first filter and a second filter; (c) illuminating at least one ultraviolet (UV) light source, wherein the at least one UV light source is positioned along an interior surface of the chamber; (d) transferring UV light through a translucent layer, wherein the translucent layer further includes or is comprised of Copper Material; (e) directing air flow through the second filter, wherein the second filter includes or is comprised of Copper Material (e.g., a copper wool layer with antimicrobial properties); (f) directing air flow through the second filter, wherein the second filter includes or is comprised of a first layer and a second layer, wherein the first layer includes or is comprised of copper wool, and wherein the second layer includes or is comprised of a textile embedded with Copper Material nanoparticles; and (g) directing air flow through a second filter, wherein the second filter includes or is comprised of a first layer and a second layer, wherein the first layer includes or is comprised of copper wool, and wherein the second layer includes or is comprised of conventional air filter material.

Referring now to the Figures.

FIG. 1 depicts one embodiment of a copper wool air filter 100 that may be useful in an air ventilation system to inactivate airborne pathogens (e.g., viruses, bacteria, coronaviruses, COVID-19, etc.) flowing through the copper wool air filter 100. In the present embodiment, copper wool air filter 100 includes or is comprised of a frame 102 and a copper wool layer 104. The frame 102 borders the perimeter of the copper wool layer 104. The copper wool layer 104 includes or is comprised of copper, or copper alloys, with antimicrobial properties. The copper wool layer 104—due to its antimicrobial properties—inactivates pathogens flowing therethrough. The copper wool layer 104 is positioned within and affixed to the frame 102. In the present embodiment, frame 102 and copper wool layer 104 are squares, wherein the perimeter of frame 102 is slightly greater than copper wool layer 104.

Alternatively, frame 102 and copper wool layer 104 may have different shapes to accommodate the dimensions of a given air ventilation system. For example, frame 102 and copper wool layer 104 may be circular, wherein the circumference of frame 102 is slightly greater than the circumference of the copper wool layer 104. As a further alternative embodiment, copper wool layer 104 may include or be comprised of two or more copper, or copper alloys, with antimicrobial properties. For example, copper wool layer 104 may include or be comprised of a combination of UNS #C10100 and C10200.

As a further alternative embodiment, copper wool air filter 100 may include or be comprised of two or more layers of copper wool. The two or more layers of copper wool may further include or be comprised of at least one copper, or copper alloy, with antimicrobial properties. The two or more layers of copper wool may have substantially similar surface area, thickness, porosity, and/or density. The two or more layer of copper wool are stacked together and positioned in a frame. For example, a first copper wool layer and a second copper wool layer with substantially similar dimensions are stacked together. The first copper wool layer and the second copper wool layer are positioned in a frame to hold the two layers in place.

Figure 2:
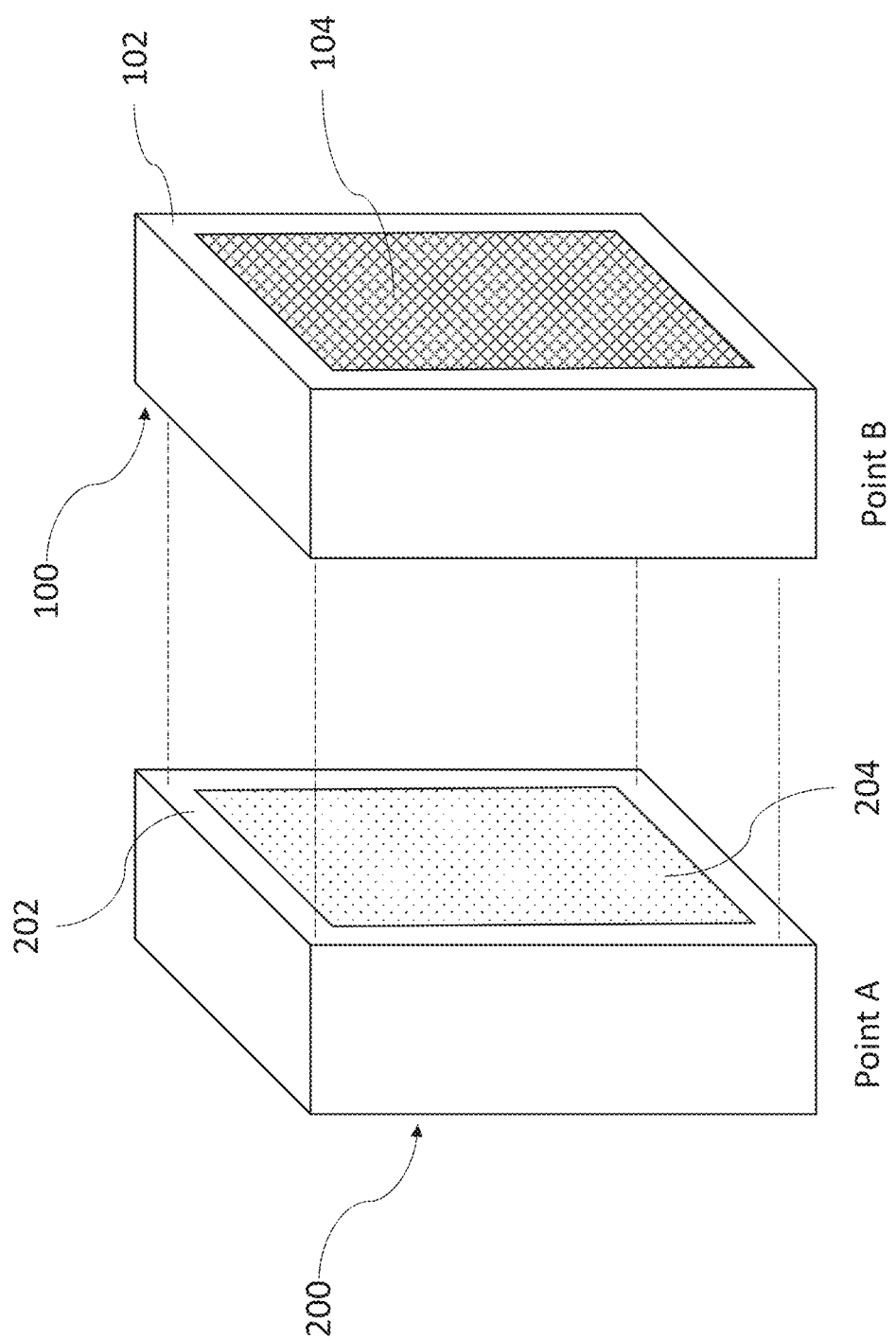
FIG. 2 depicts an air filtration system, which utilizes a conventional air filter accompanied by the copper wool air filter of FIG. 1, according to an embodiment of the present disclosure.

FIG. 2 depicts one embodiment wherein the copper wool air filter 100 having frame 102 bordering the perimeter of the copper wool layer 104 is positioned adjacent to a conventional air filter 200. In the present embodiment, the conventional air filter 200 is a HEPA filter used in air ventilation systems. Other types of conventional air filters may also be useful. Conventional air filter 200 includes or is comprised of a conventional frame 202 and a HEPA filter layer 204. Dimensions of conventional air filter 200 and copper wool air filter 100 are substantially similar. Copper wool air filter 100 is positioned downstream of airflow with respect to conventional air filter 200. Copper wool air filter 100 is affixed to conventional air filter 200 through mechanical means (not shown; e.g., screws). The dimensions of conventional filter and copper wool air filter do not need to be same or about same.

Alternatively, copper wool air filter 100 is not affixed to conventional air filter 200 and, rather, is affixed to a ventilation structure (not shown) either without a conventional air filter, or upstream or downstream of airflow with respect to conventional air filter 200. For example, a ventilation duct of an air filtration system may include conventional air filter 200 positioned along the ventilation duct at Point A and may include copper wool air filter 100 positioned along the ventilation duct at Point B. The distance between Point A and Point B (i.e., between conventional air filter 200 and copper wool air filter 100) is greater than 0 inches. In other embodiments, copper wool air filter 100 may be disposed upstream relative to conventional air filter 200.

Figure 3:
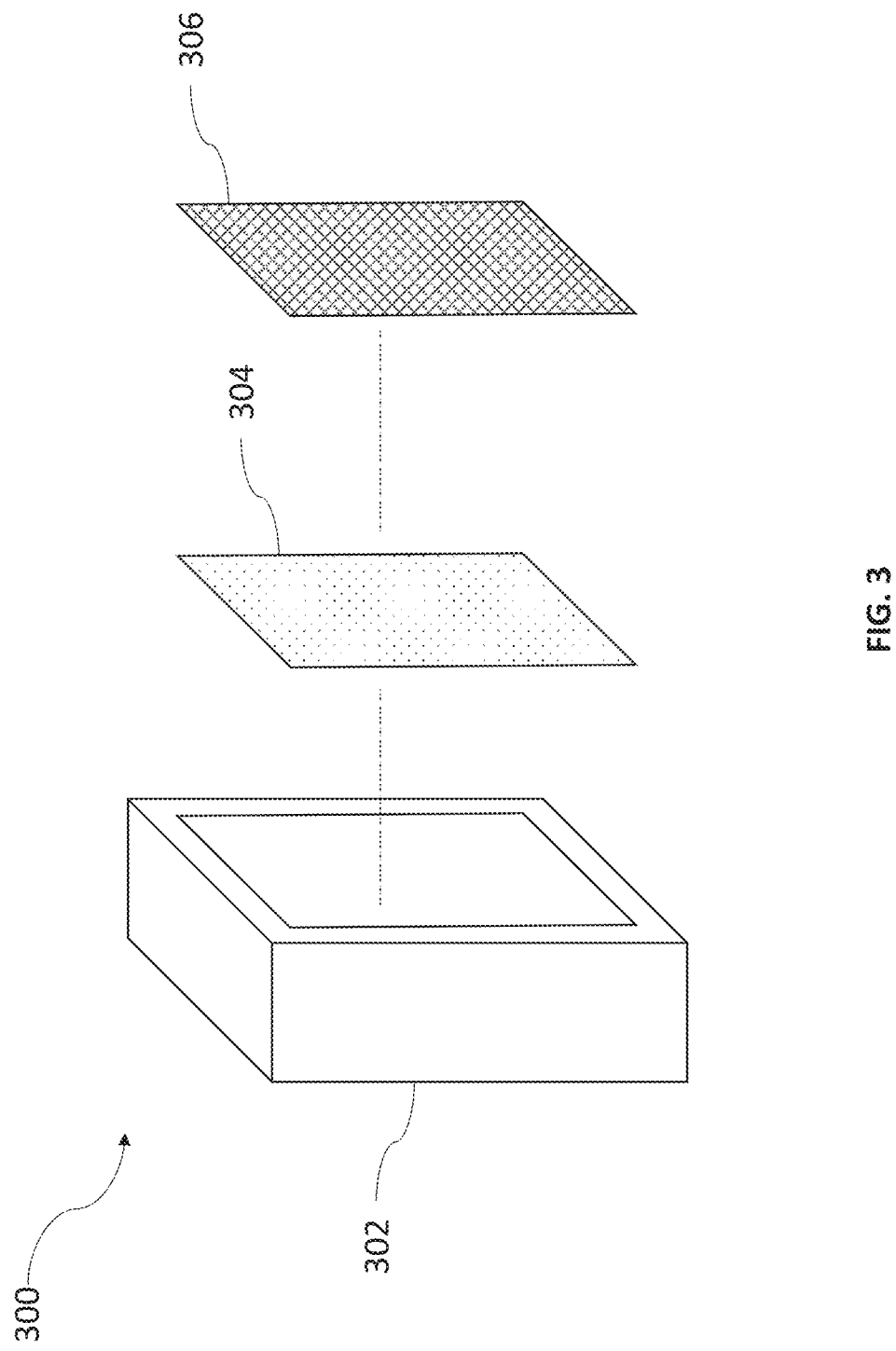
FIG. 3 depicts an air filter having or comprised of a copper wool medium and a conventional air filter medium, according to an embodiment of the present disclosure.

FIG. 3 depicts an exploded view of a hybrid air filter 300 that may be used in an air ventilation system to inactivate airborne pathogens (e.g., viruses, bacteria, coronaviruses, COVID-19, etc.) flowing through the hybrid air filter 300. In the present embodiment, hybrid air filter 300 includes or is comprised of a filter frame 302 and two filter layers. A first filter layer 304 includes or is comprised of a conventional filter material used to create a conventional air filter, such as a HEPA filter. A second filter layer 306 includes or is comprised of copper wool, wherein the copper wool is a copper, or copper alloy, that has antimicrobial properties. The first filter layer 304 and the second filter layer 306 are stacked together, such that the second filter layer 306 is positioned downstream of airflow with respect to the position of the first filter layer 304. The first filter layer 304 and the second filter layer 306 are positioned within, and held by, filter frame 302. Filter frame 302 is a rigid structure with a substantial portion of its surface area removed, such that the surface area of the first filter layer 304 and the second filter layer 306 cover the entirety of the surface area that is removed from filter frame 302. The first filter layer 304 and second filter layer 306 may be held in place through mechanical means by filter frame 302. Filter frame 302 may be configured to direct an air stream through the first filter layer 304 and through the second filter layer 306.

Alternatively, second filter layer 306 includes or is comprised of two or more copper, or copper alloys, with antimicrobial properties. For example, second filter layer 306 includes or is comprised of copper wool with a first copper composition and a plurality of nanoparticles with a second copper composition positioned on the copper wool.

As a further alternative embodiment, hybrid air filter 300 may include or be comprised of three or more layers, wherein at least two layers include or are comprised of copper wool. For example, an air filter includes or is comprised of three layers. A HEPA filter layer, a first copper wool layer, and a second copper wool layer. The three layers are stacked together such that the first copper wool layer and the second copper wool layer are positioned downstream of air flow with respect to the position of the HEPA filter layer.

As a further alternative embodiment, hybrid air filter 300 includes or is comprised of two layers. A first layer is a textile with copper, or copper alloy, nanoparticles. A second layer is copper wool. The first layer and the second layer are stacked together and positioned within a frame, such that the second layer is positioned downstream of airflow with respect to the position of the first layer.

FIG. 4 depicts one embodiment of a face mask device 400 that is worn by a living organism to inactivate airborne pathogens (e.g., viruses, bacteria, coronaviruses, COVID-19, etc.) flowing through the face mask device 400 during respiratory functions (i.e., breathing). In the present embodiment, face mask device 400 includes or is comprised of three layers: an inner layer 402, a middle layer 404, and an outside layer 406. Inner layer 402 and outside layer 406 include or are comprised of a textile. Middle layer 404 includes or is comprised of copper wool. The copper wool is one or more copper, or copper alloys, with antimicrobial properties. Middle layer 404 is positioned between inside layer 402 and outside layer 404. The three layers are stacked together and affixed to each other by one or more mechanisms (e.g., sewn together). The face mask device 400 device may have one or more straps (not shown) to hold face mask device 400 in a position such that a user's airflow (i.e., inhale and exhale) passes through the face mask device 400. Any pathogens, such as COVID-19, are inactivated by the middle layer 404.

Alternatively, inner layer 402 and/or outer layer 406 include or are comprised of a textile with copper, or copper alloy, nanoparticles embedded within the textile. For example, an outer layer of a face mask device includes or is comprised of a textile with copper oxide nanoparticles.

As a further alternative embodiment, a copper wool layer may be positioned on the outside surface and/or the inside surface of face mask device 400.

FIG. 5A depicts a side view of one embodiment of a face mask device 500 that is worn by a living organism to inactivate airborne pathogens (e.g., viruses, bacteria, coronaviruses, COVID-19, etc.) flowing through the face mask device 500 during respiratory functions (i.e., breathing). In the present embodiment, face mask device 500 includes or is comprised of an outer layer 502 and an ear strap 504. Outer layer 502 further includes or is comprised of a textile and has dimensions substantially similar to the shape of a human face. A detachable filter 506 is positioned on outer layer 502, such that the airflow (i.e., inhale and exhale) passes through the detachable filter 506. The detachable filter 506 includes or is comprised of copper wool and is affixed to the outer layer 502 through mechanical means (e.g., snap on, screw on, etc.). The detachable filter 506 is removable so that the copper wool can be replaced after use to maintain efficiency in preventing the transmission of pathogens.

Alternatively or additionally, outer layer 502 is a textile having or comprised of copper, or copper alloy, nanoparticles.

As a further alternative embodiment, detachable filter 506 includes or is comprised of two or more filter layers, wherein at least one of the two or more filter layers includes or is comprised of copper wool. For example, a face mask device has a detachable filter positioned on an outer surface. The detachable filter has a rigid structure with a first layer and a second layer positioned within the rigid structure. The first layer is a textile and the second layer is copper wool.

Figure 5B:
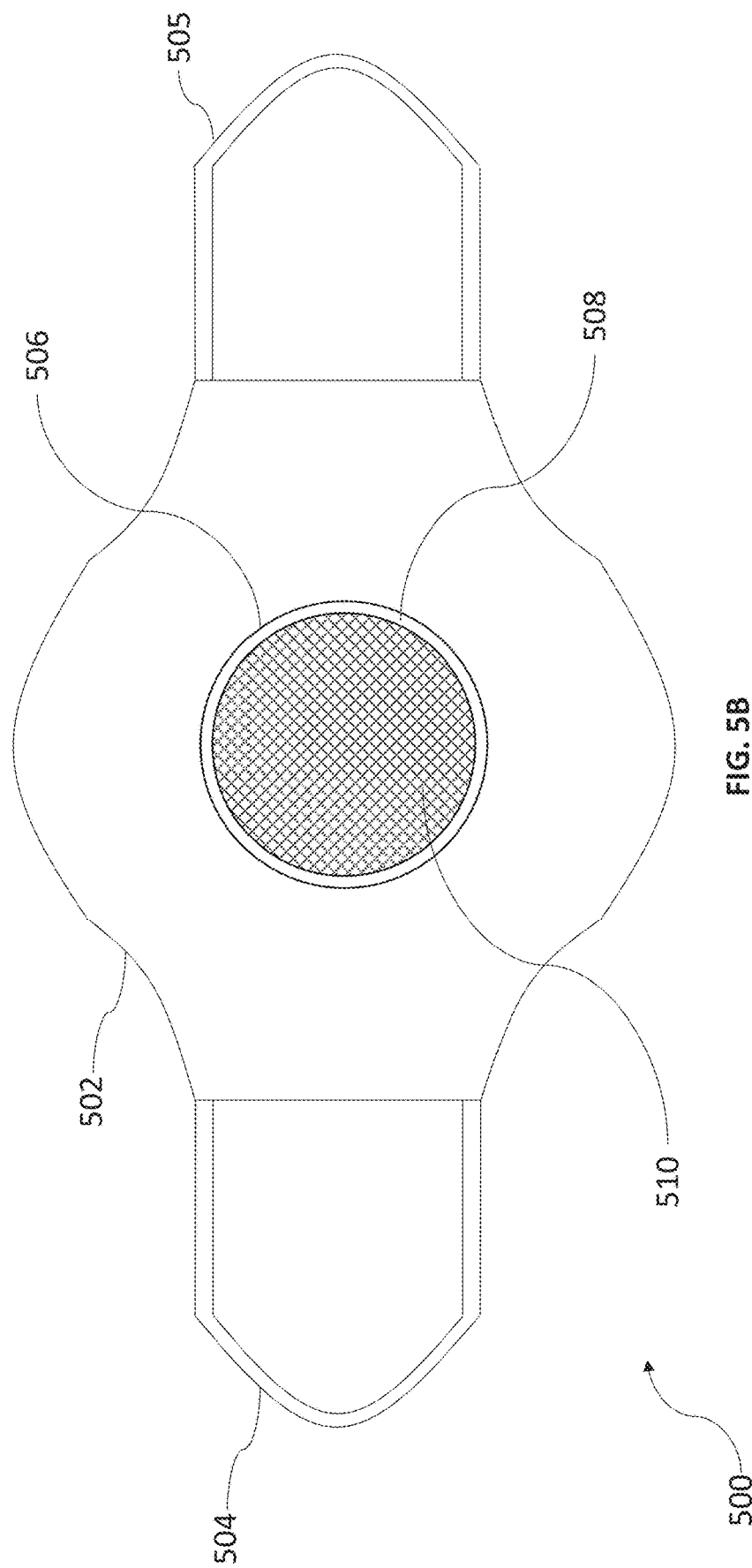
FIG. 5B depicts a front view of the face mask device of FIG. 5A, according to an embodiment of the present disclosure.

FIG. 5B depicts a front view of the face mask device 500 (see FIG. 5A). In the present embodiment, face mask device 500 further includes or is comprised of a second ear strap 505 positioned opposite the ear strap 504. Detachable filter 506 further includes or is comprised of a detachable frame 508 that supports a copper wool medium 510 positioned on outer layer 502. The detachable filter 506 is configured to direct airflow (i.e., inhale and exhale) through the copper wool medium 510.

As a further alternative embodiment, the detachable filter 506 may be permanently affixed to the face mask device 500.

Figure 5C:
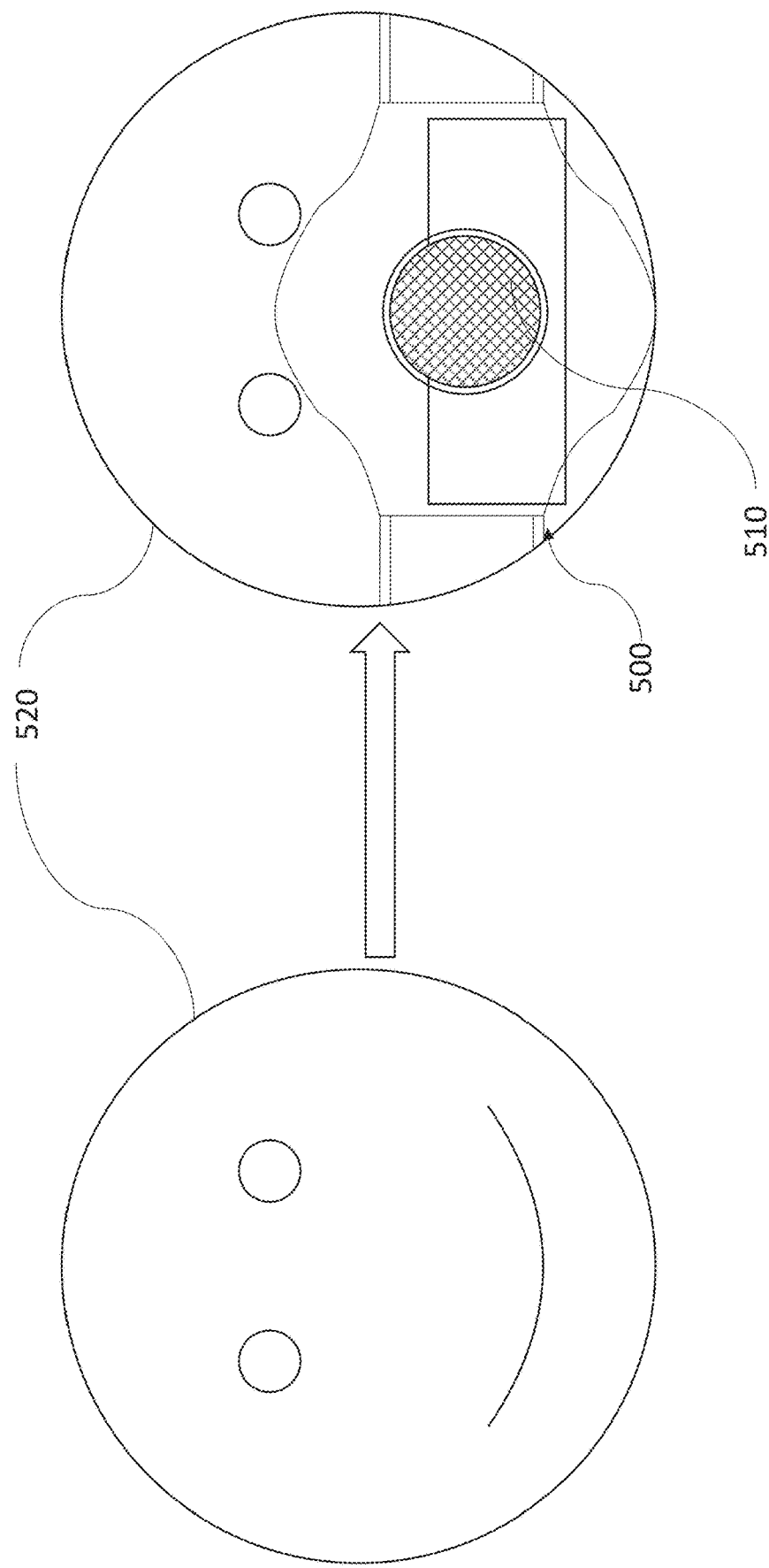
FIG. 5C depicts a front view of the face mask device of FIG. 5A positioned on a human face, according to an embodiment of the present disclosure.

FIG. 5C depicts a front view of the face mask device 500 (see FIG. 5A and FIG. 5B) in use. In the present embodiment, a person 520 is shown without wearing the face mask device 500 and wearing the face mask device 500. The ear strap 504 and second ear strap 505 affix the face mask device 500 to the face of person 520. The face mask device 500 is positioned on the face of person 520 such that respiratory functions (i.e., breathing) direct the airflow through the copper wool medium 510. The copper wool medium 510 includes or is comprised of a copper, or copper alloys, or Copper Material that inactivate pathogens (such as coronaviruses) and mitigate the risk of pathogen transmission during respiratory functions.

For example, a first person wearing face mask device 500 may be disposed less than 6 feet away from a second person who is not wearing any face mask. The second person has COVID-19 and releases COVID-19 virus particles into the airflow that the first person is inhaling. The airflow—containing COVID-19 virus particles—are inhaled by the first person through the copper wool medium 510 of face mask device 500. The copper wool medium 510 inactivates the COVID-19 virus particles prior to inhalation. As such, COVID-19 is inactive upon inhalation and is not transmitted to the first person.

Figure 6A:
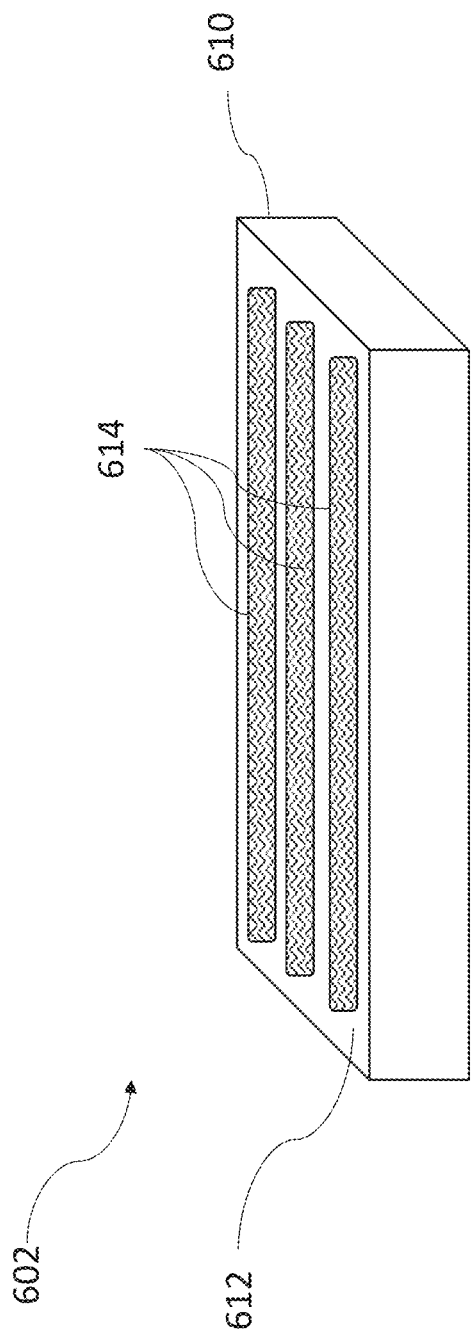
FIG. 6A depicts an ultraviolet light source panel to purify air, according to an embodiment of the present disclosure.

FIG. 6A depicts a chamber panel 602 that may be useful to inactivate airborne pathogens (e.g., viruses, bacteria, coronaviruses, COVID-19, etc.) flowing through a ventilation system. In the present embodiment, chamber panel 602 includes a panel base 610, wherein the panel base is a durable structure that can be affixed to one or more similar chamber panels and/or one or more air filters. Panel base 610 is a rectangle with a top surface 612; other dimensions may be useful as well. A plurality of UV light sources 614 are affixed to the top surface 612. The plurality of UV light sources 614 are oriented to disperse ultraviolet light away from top surface 612.

Alternatively, a single UV light source is affixed to top surface 612.

As a further alternative embodiment, the plurality of UV light sources 614 may be positioned within panel base 610 through top surface 612. A translucent layer (not shown) may be positioned over top surface 612. The translucent layer (not shown) may include or be comprised of copper, or copper alloy, nanoparticles.

Figure 6B:
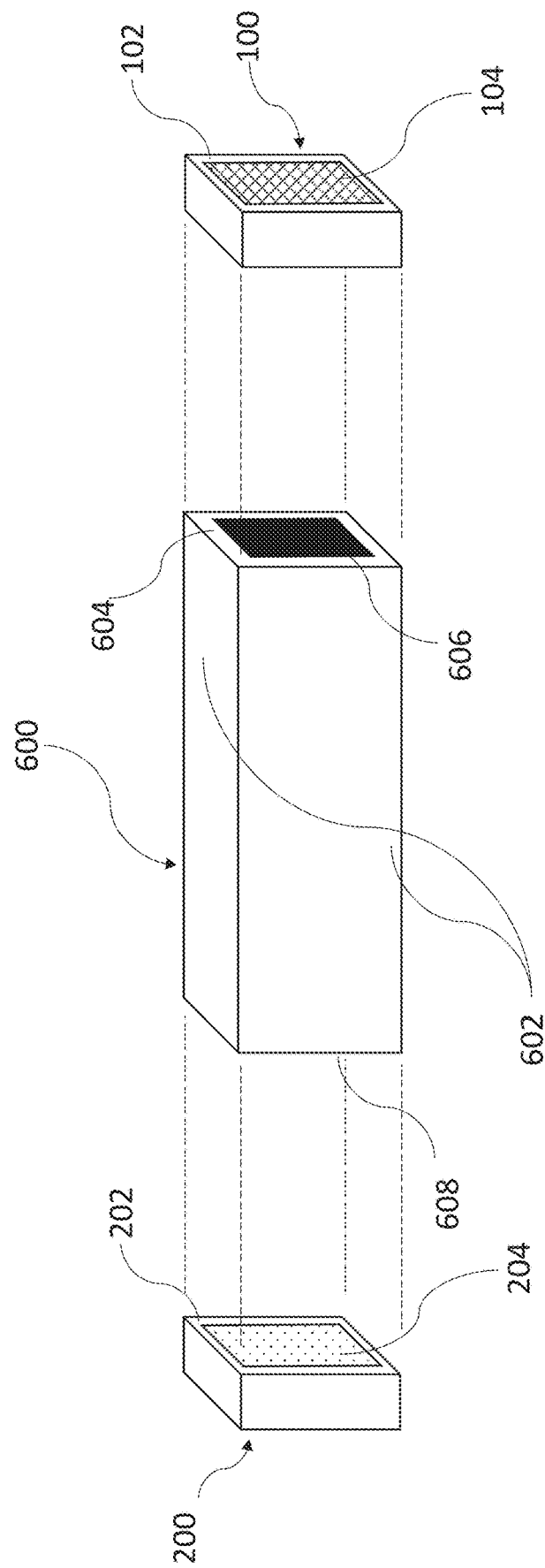
FIG. 6B depicts an air filtration system that utilizes a combination of a conventional air filter, a plurality of the ultraviolet light source panels of FIG. 6A, and a copper wool air filter, according to an embodiment of the present disclosure.

FIG. 6B depicts an exploded view of one embodiment of a UV ventilation chamber 600 device to inactivate airborne pathogens (e.g., viruses, bacteria, coronaviruses, COVID-19, etc.) flowing therethrough. In the present embodiment, UV ventilation chamber 600 is a rectangle having or comprised of a plurality of chamber panels 602 on four faces. Chamber panels 602 are rectangles that have or are comprised of at least one UV light sources 614 (see FIG. 6A) that radiate ultraviolet light within the UV ventilation chamber 600. Four chamber panel 602 structures connect to form a first chamber face 604 and a second chamber face 608. A first aperture 606 is positioned on the first chamber face 604, such that the dimensions of first aperture 606 are based, at least in part, on the thickness of panel base 610 (see FIG. 6A) of chamber panel 602. A second aperture (not shown) is positioned on the second chamber face 608. A channel extends between first aperture 606 and the second aperture (not shown) positioned opposite the first aperture 606. The first aperture 606 and the second aperture (not shown) are in fluid communication with each other (i.e., air flow can pass through the second aperture through the channel along the length of chamber panel 602 and through the first aperture 606). Conventional air filter 200 (see FIG. 2) may be affixed to one end of UV ventilation chamber 600, and copper wool air filter 100 (see FIG. 1) may be affixed to the opposite end of UV ventilation chamber 600. As shown, copper wool air filter 100 is affixed to the first chamber face 604 such that copper wool layer 104 is aligned with first aperture 606. Likewise, conventional air filter 200 is affixed to the second chamber face 608 such that the HEPA filter layer 204 is aligned with the second aperture (not shown).

UV ventilation chamber 600, conventional air filter 200, and copper wool air filter 100 (collectively, hereinafter referred to as "UV and Copper Ventilation Structure") may be positioned within an air ventilation system to inactivate airborne pathogens (e.g., viruses, bacteria, coronaviruses, COVID-19, etc.) flowing therethrough. The UV and Copper Ventilation Structure is oriented such that the copper wool air filter 100 is positioned downstream of airflow relative to conventional air filter 200. An air stream flows through conventional air filter 200 through UV ventilation chamber 600 and through copper wool air filter 100. During use, at least one UV light source 614 (see FIG. 6A) radiates ultraviolet light from at least one chamber panel 602. The ultraviolet radiating from the at least one UV light source 614 (see FIG. 6A) deteriorates/inactivates one or more airborne pathogens passing through the UV ventilation chamber 600. As such, the air stream is purified and airborne pathogens are inactivated at three stages to mitigates the risk of pathogen transmission (i.e., pathogens are removed by the HEPA filter 204, deteriorated by UV light radiating from the plurality of chamber panels 602, and inactivated by the copper wool layer 104).

As a further alternative embodiment, hybrid air filter 300 (see FIG. 3) may be positioned on either end of UV ventilation chamber 600.

Figure 6C:
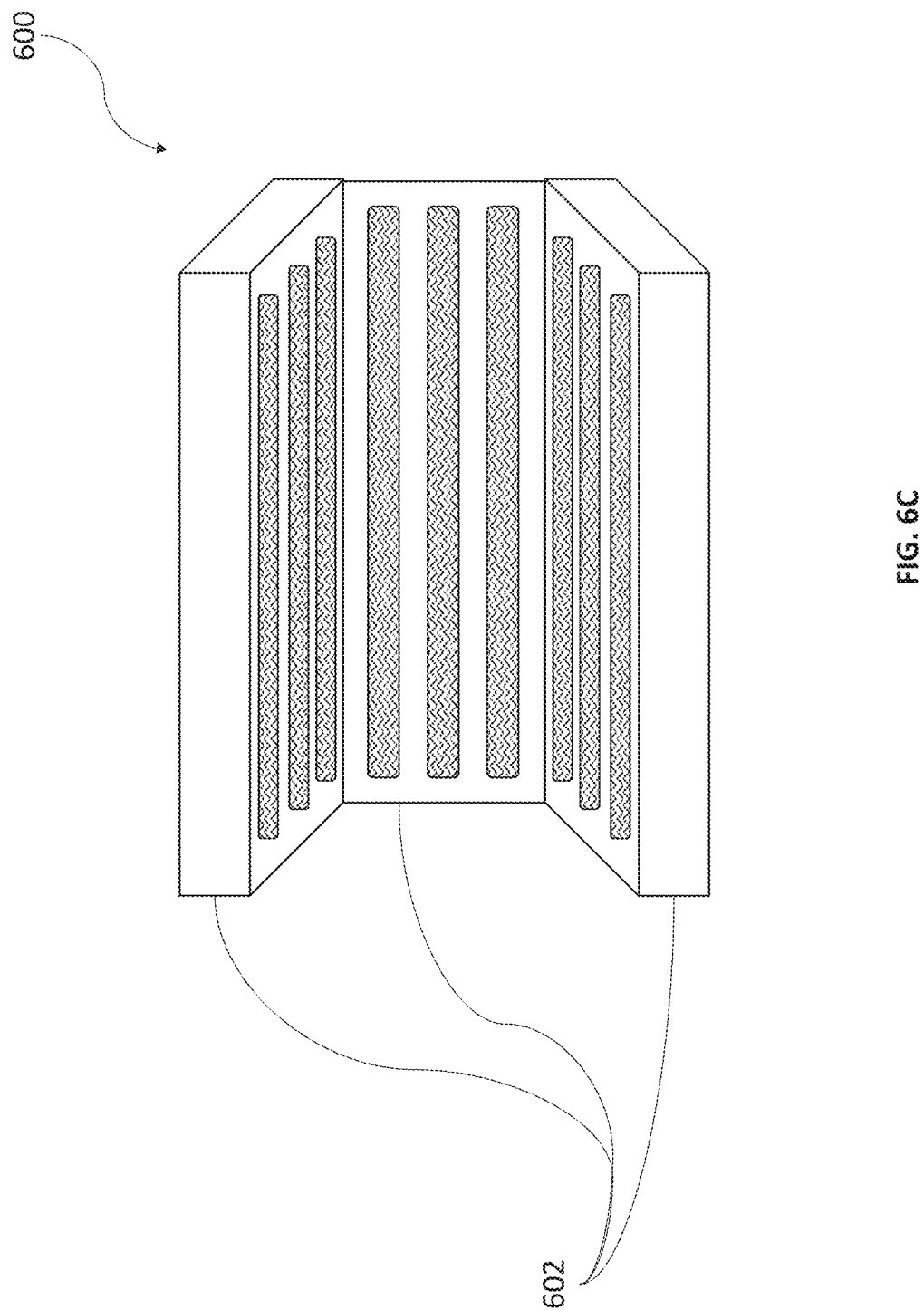
FIG. 6C depicts a plurality of the ultraviolet light source panels of FIG. 6A according to an embodiment of the present disclosure.

FIG. 6C depicts a cross-sectional view of UV ventilation chamber 600. In the present embodiment, three chamber panels 602 are shown as described in FIG. 6A. The fourth chamber panel is omitted to show the interior structure of UV ventilation chamber 600 (see FIG. 6B). Alternative configurations may include different quantities of ultraviolet light sources; different orientation of ultraviolet light sources; limiting the amount of ultraviolet light sources such that less than four faces of the interior chamber include or are comprised of ultraviolet light sources; or changing the dimensions of UV ventilation chamber 600 (see FIG. 6B) (e.g., a cylindrical channel with a plurality of ultraviolet light sources positioned along the interior surface of the cylindrical channel). The ultraviolet light sources may include, but not limited to different ultraviolet light frequencies.

Figure 7:
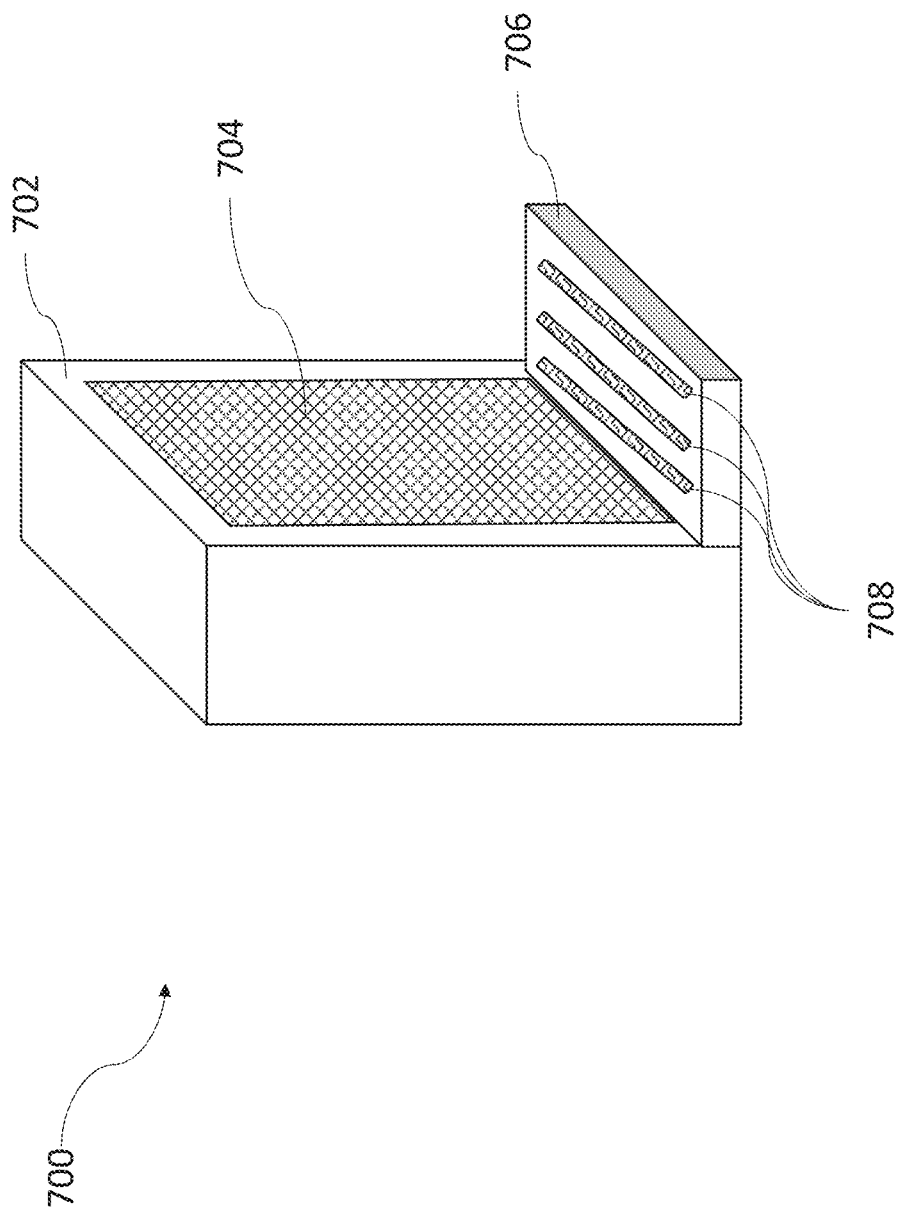
FIG. 7 depicts an air filter with a copper wool medium and an ultraviolet light source use in combination to disinfect air particles, according to an embodiment of the present disclosure.

FIG. 7 depicts one embodiment of an ultraviolet air filter device 700 to inactivate airborne pathogens (e.g., viruses, bacteria, coronaviruses, COVID-19, etc.) from an air stream flowing therethrough. In the present embodiment, ultraviolet air filter device 700 includes or is comprised of a frame 702 with four elongate sides connected at corners. A copper wool medium 704 is positioned such that the frame 702 borders the perimeter of the copper wool medium 704. The copper wool medium 704 includes or is comprised of porous copper, or copper alloys, with antimicrobial properties. Frame 702 provides structural rigidity to the copper wool medium 704 and directs an air stream in a ventilation system to flow through the copper wool medium 704. A light panel 706 is affixed to one elongate side of the frame 702. The light panel 706 includes or is comprised of a plurality of UV light sources 708. The plurality of UV light sources 708 disperse ultraviolet light in a direction such that air stream flowing through copper wool medium 704 is contacted by ultraviolet light. The ultraviolet air filter device 700 may be oriented such that the UV light sources 708 are either downstream or upstream relative to the copper wool medium 704. Although light panel 706 includes or is comprised of a plurality of UV light sources 708 as shown, any number of UV light sources (i.e., one or more) may be useful.

Figure 8A:
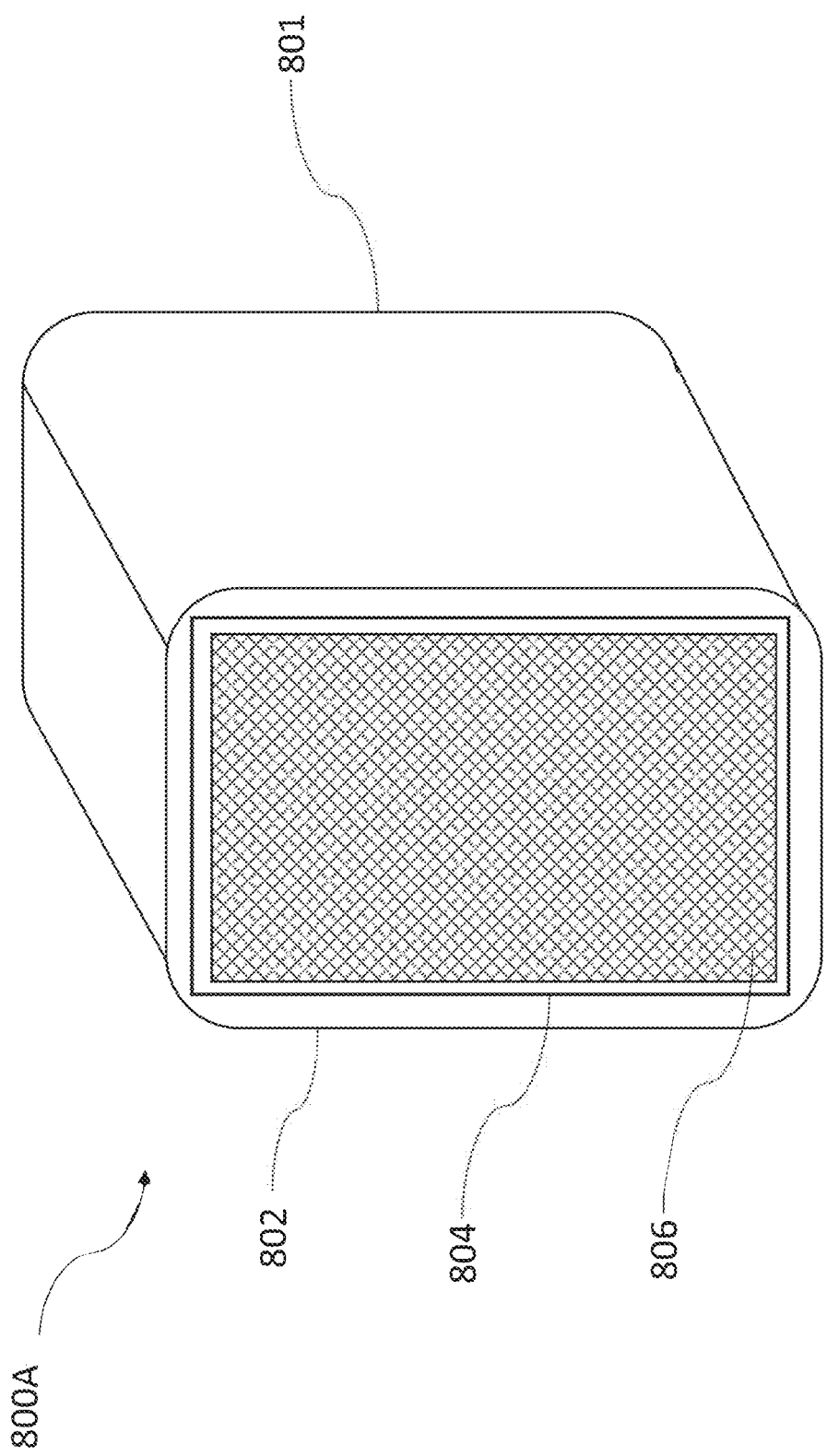
FIG. 8A depicts a humidity device with a copper wool medium, according to an embodiment of the present disclosure.
Figure 8B:
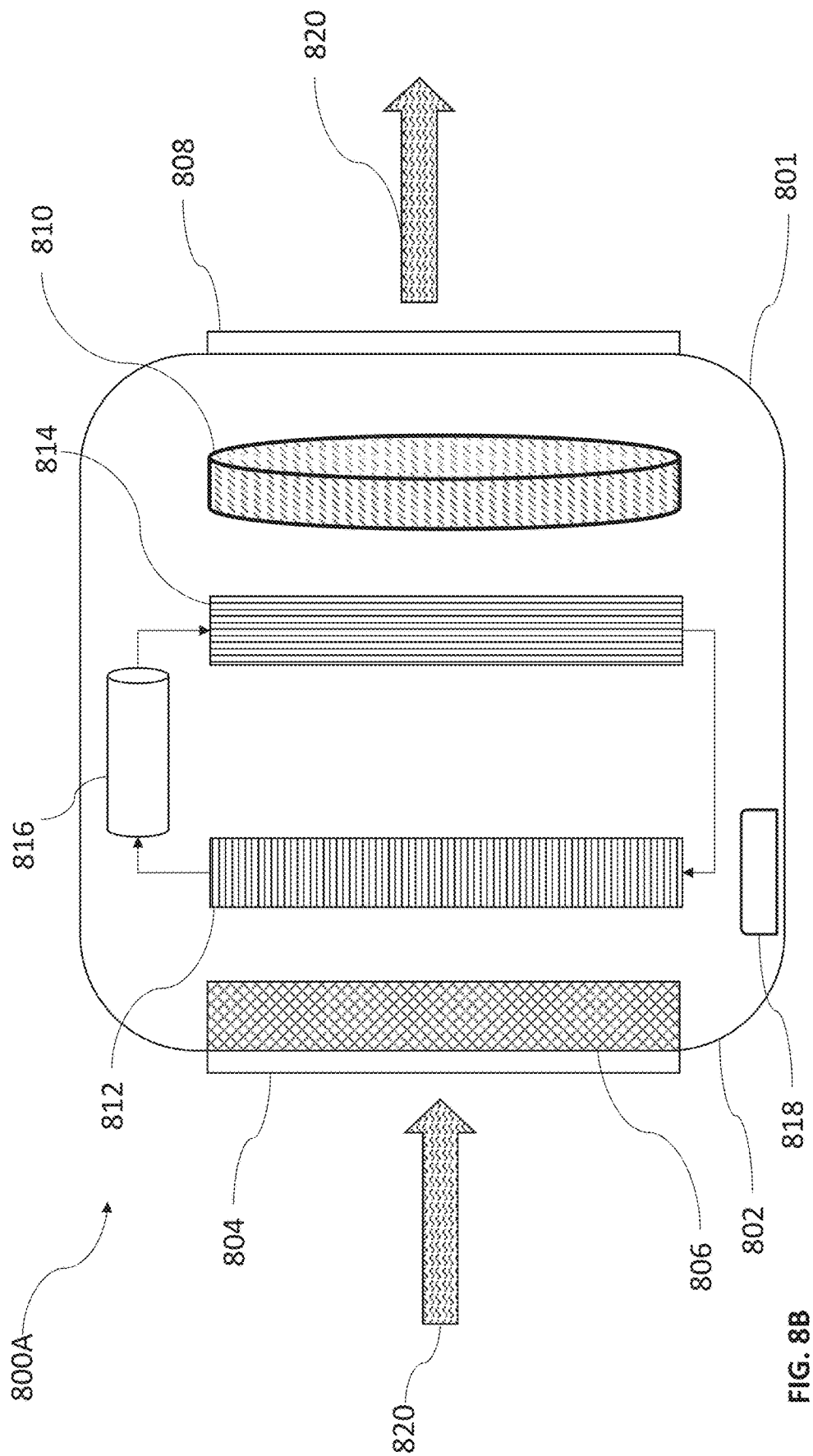
FIG. 8B depicts a cross-sectional side view of the humidity device of FIG. 8A, according to an embodiment of the present disclosure.
Figure 9A:
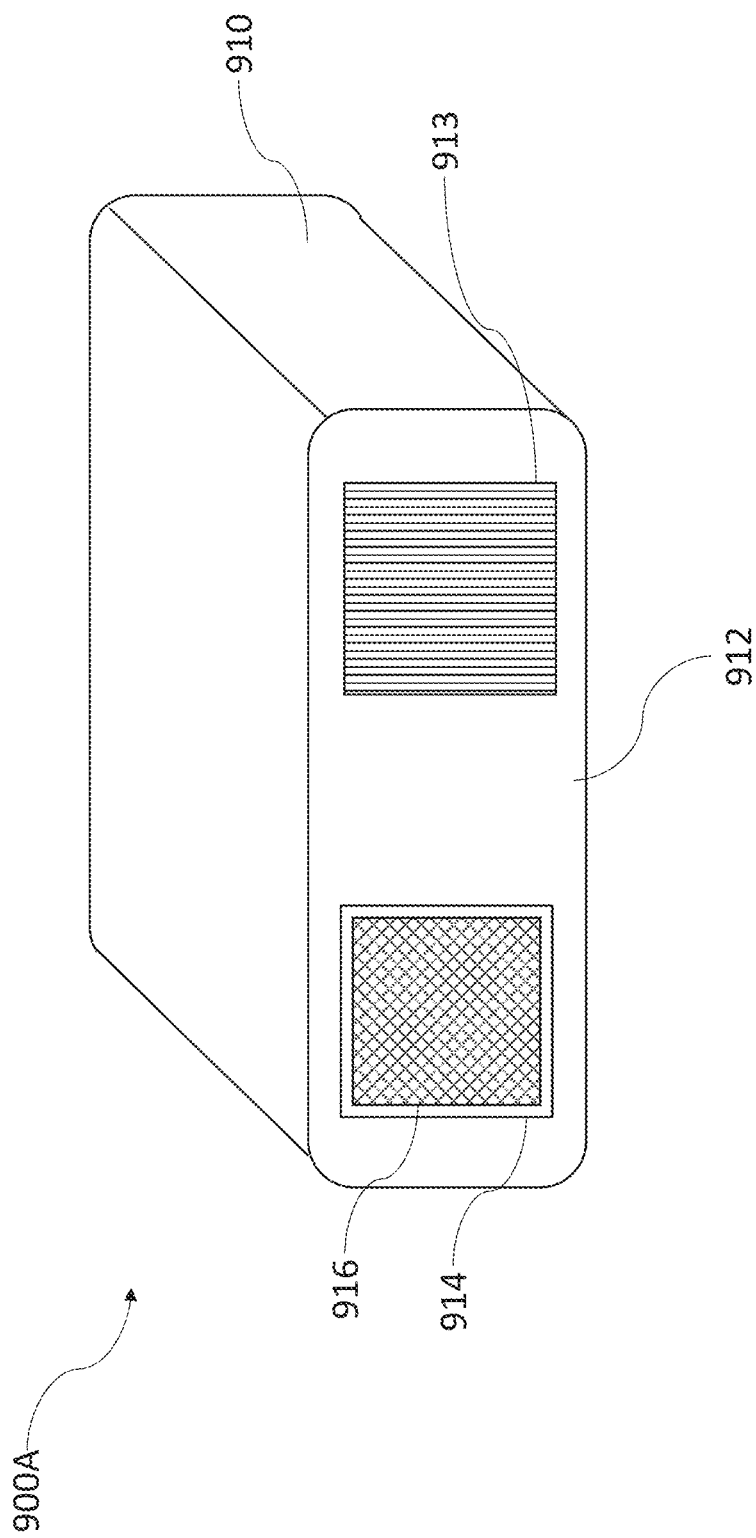
FIG. 9A depicts an air purifier device with a copper wool medium, according to an embodiment of the present disclosure.
Figure 9B:
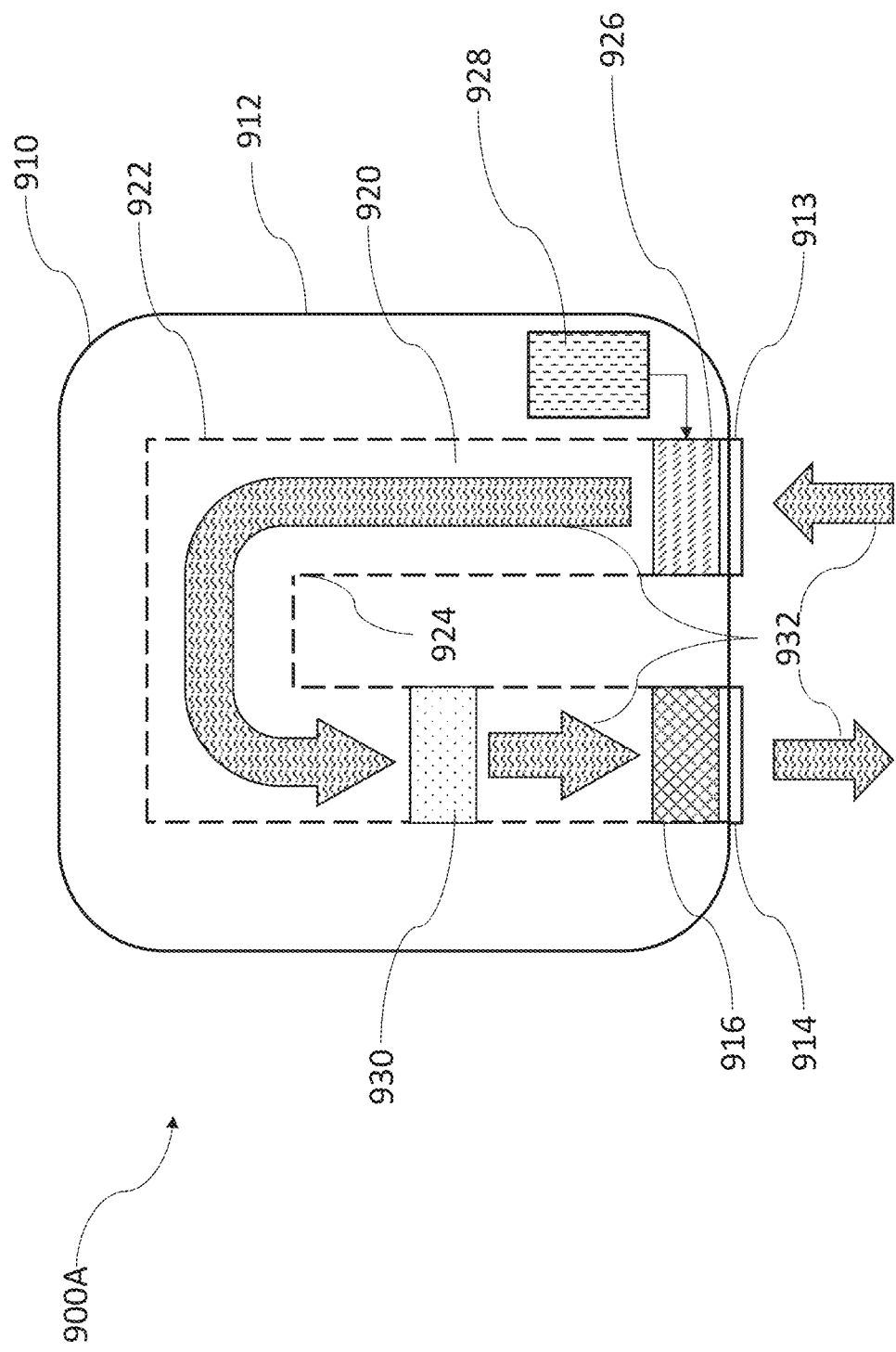
FIG. 9B depicts a cross-sectional top view of the air purifier device of FIG. 9A, according to an embodiment of the present disclosure.
Figure 10:
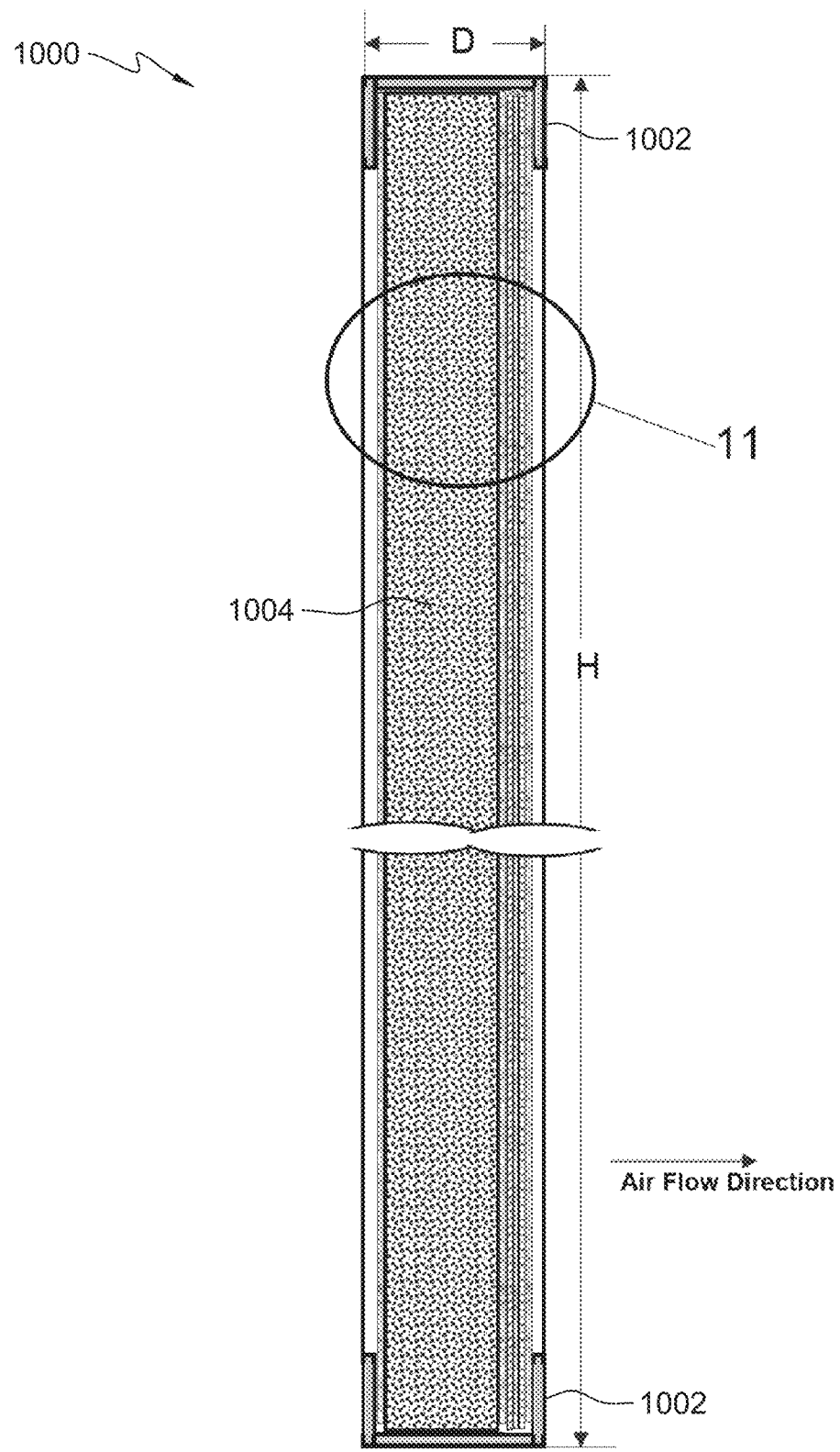
FIG. 10 depicts a hybrid air filter, according to an embodiment of the present disclosure.
Figure 11:
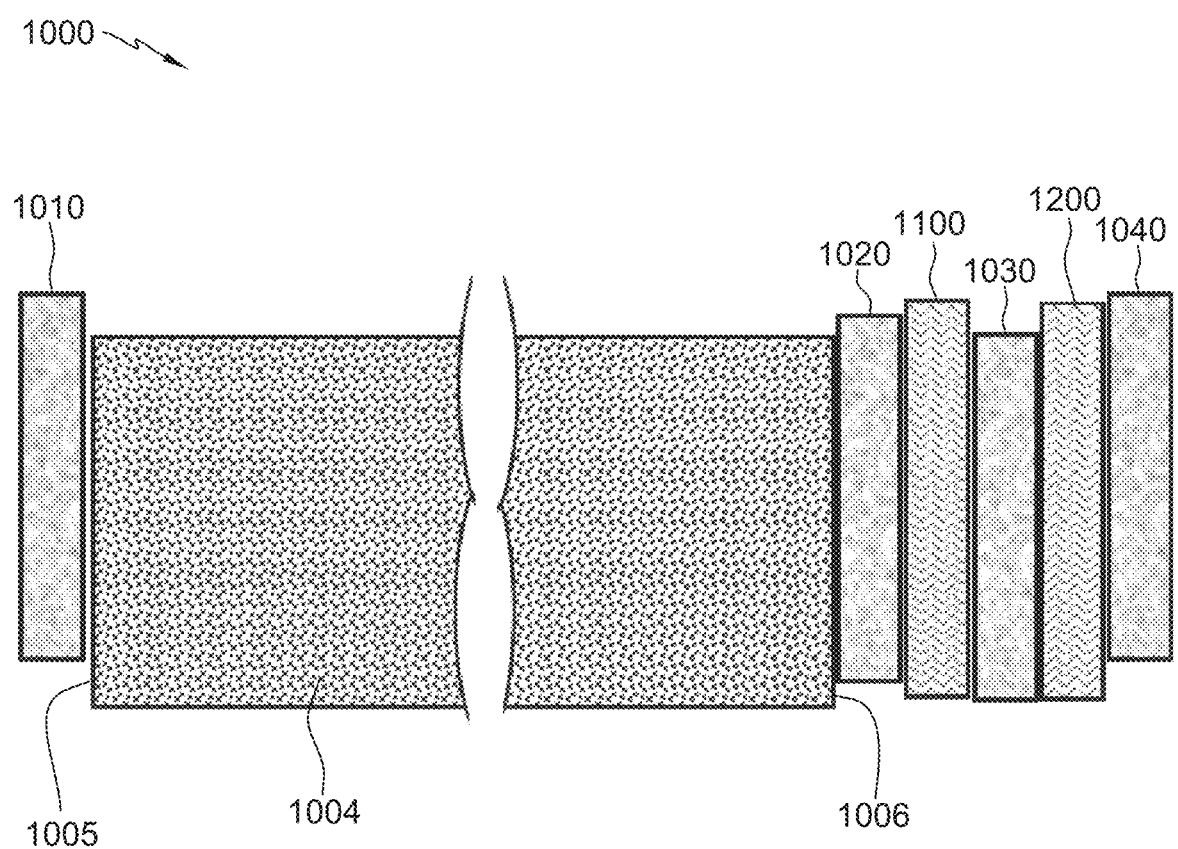
FIG. 11 is an enlarged detail 11 of FIG. 10, according to an embodiment of the present disclosure.

FIG. 8A depicts one embodiment of a humidity device 800A that may be useful to inactivate airborne pathogens (e.g., viruses, bacteria, coronaviruses, COVID-19, etc.) in an air stream flowing therethrough. In the present embodiment, humidity device 800A includes or is comprised of a device body 801 with a first surface 802, wherein device body 801 is configured to add or remove moisture from an air stream flowing therethrough (e.g., dehumidifier or humidifier). Device body 801 includes or is comprised of one or more internal components (see FIG. 8B) configured to add or remove moisture from the air stream. Humidity device 800A is configured to direct an air stream through an airflow inlet 804 positioned on first surface 802, through an internal configuration of the device body 801 (see FIG. 8B), and through an airflow outlet 808 (see FIG. 8B) positioned on a second surface of device body 801 (see FIG. 8B). Humidity device 800A is configured to direct an air stream through a copper wool medium 806, wherein copper wool medium 806 is positioned on, or proximate to, first surface 802. It follows that a plurality of air particles in the air stream flowing therethrough contact copper wool medium 806.

Airborne pathogens within an air stream flowing through humidity device 800A are inactivated upon contact with the copper wool medium 806.

Alternatively, or additionally, humidity device 800A includes or is comprised of a conventional air filter and a copper wool medium (see FIG. 2 and FIG. 3). Humidity device 800A is configured to direct an air stream through a conventional air filter and through a copper wool medium. One or more internal components (see FIG. 8B) of humidity device 800A control the addition, or removal, of moisture from an air stream flowing therethrough (e.g., dehumidifier or humidifier).

FIG. 8B depicts a cross-sectional side view of one embodiment of humidity device 800A that may be useful to inactivate airborne pathogens (e.g., viruses, bacteria, coronaviruses, COVID-19, etc.) in an air stream flowing therethrough. In the present embodiment, humidity device 800A is a dehumidifier configured to remove moisture from an air stream 820 flowing therethrough. Device body 801 includes or is comprised of an air flow outlet 808 positioned on a surface opposite airflow inlet 804. Device body 801 further includes or is comprised of a plurality of internal components to remove moisture from air stream 820 flowing therethrough, wherein the plurality of components includes an airflow fan 810, a cold source 812, a heat source 814, a compressor 816, and a water tray 818. Humidity device 800A may be connected to an internal or external power source (not shown) to operate one or more components of a plurality of components within device body 801. Humidity device 800A is configured to direct an air stream 820 through airflow inlet 804 through copper wool medium 804 through cold source 812 through heat source 814 through airflow fan 810 and through airflow outlet 808. Cold source 812 is configured to decrease the temperature of air stream 820, wherein the decrease of temperature results in the removal of water from air stream 820 and stored in water tray 818. Heat source 814 is configured to increase the temperature of air stream 820, wherein heat source 814 is positioned downstream of cold source 812. Compressor 816 is configured to enable fluid communication between cold source 812 and heat source 814, wherein compressor 816 circulates a refrigerant (not shown) through cold source 812 and through heat source 814. It follows that air stream 820 is directed through airflow inlet 804; airborne pathogens within air stream 820 are inactivated upon contact with copper wool medium 806; the temperature of air stream 820 decreases from contact with cold source 812 and removes water from air stream 820; the temperature of air stream 820 increases from contact with heat source 814; air stream 820 is directed through airflow fan 810 and through airflow outlet 808.

Alternatively, or additionally, humidity device 800A of FIG. 8B includes or is comprised of internal components configured to add moisture to an air stream flowing therethrough (e.g., humidity device 800A is a humidifier).

FIG. 9A depicts one embodiment of an air purifier device 900A that may be useful to inactivate airborne pathogens (e.g., viruses, bacteria, coronaviruses, COVID-19, etc.) in an air stream flowing therethrough. In the present embodiment, air purifier device 900A includes or is comprised of a body 910, wherein the body 910 includes or is comprised of an outer surface 912 and an internal configuration (see FIG. 9B). An airflow inlet 913 and an airflow outlet 914 are positioned on outer surface 912, wherein airflow inlet 913 and airflow outlet 914 are configured to be in fluid communication through an internal configuration (see FIG. 9B) of body 910. The air purifier device 900A is configured to direct an air stream through airflow inlet 913, through an internal configuration (see FIG. 9B) of body 910, and through airflow outlet 914. Airflow outlet 914 further includes or is comprised of a copper wool medium 916 positioned on, or proximate to, outer surface 912. Airflow outlet 914 is configured to direct an air stream through copper wool medium 916. It follows that a plurality of air particles in an air stream directed through air purifier device 900A contact copper wool medium 916. Airborne pathogens within an air stream flowing through air purifier device 900A are inactivated upon contact with the copper wool medium 916.

Alternatively, or additionally, air purifier device 900A includes or is comprised of a conventional air filter and a copper wool medium (see FIG. 2 and FIG. 3). An internal configuration (see FIG. 9B) of air purifier device 900A is configured to direct an air stream through the conventional air filter and through the copper wool medium.

FIG. 9B depicts a cross-sectional top view of one embodiment of an internal configuration of air purifier device 900A that may be useful to inactivate airborne pathogens (e.g., viruses, bacteria, coronaviruses, COVID-19, etc.) in an air stream flowing therethrough. In the present embodiment, air purifier device 900A includes or is comprised of an airflow channel 920, wherein airflow channel 920 enables fluid communication between airflow inlet 913 and airflow outlet 914 through body 910. Airflow channel 920 includes or is comprised of a first airflow channel wall 922 and a second airflow channel wall 924. An airflow fan 926 is positioned along airflow channel 920, wherein airflow fan 926 is configured to direct an air stream 932 into body 910 through airflow inlet 913. Airflow fan 926 is connected to a power source 928, wherein power source 928 is configured to transfer energy to rotate airflow fan 926. A conventional air filter 930 (e.g., HEPA filter) is positioned along airflow channel 920, wherein conventional air filter 930 is configured to prevent large air particles (not shown) in air stream 932 from leaving airflow channel 920. Airflow channel 920 is configured to direct air stream 932 through airflow inlet 913 through conventional air filter 930 through copper wool medium 916 and through airflow outlet 914. It follows that a plurality of air particles in air stream 932 directed through air purifier device 900A contact copper wool medium 916. Airborne pathogens within air stream 932 flowing through air purifier device 900A are inactivated upon contact with copper wool medium 916.

FIG. 10 depicts a hybrid air filter 1000 that may be used in an air ventilation system to inactivate airborne pathogens (e.g., viruses, bacteria, coronaviruses, COVID-19, etc.) flowing through the hybrid air filter 1000. In the present embodiment, hybrid air filter 1000 includes or is comprised of a filter frame 1002, a filter 1004, and a plurality of screen layers. Hybrid air filter 1000 may have an overall thickness or depth D of about 1 inch. Hybrid air filter 1000 may have a height H of about 16 inches. Hybrid air filter 1000 may square having a width of about 16 inches. It will be appreciated that hybrid filter my have any suitable configuration.

As illustrated in FIG. 11, filter 1004 includes or is comprised of a conventional filter material used to create a conventional air filter, such as a MERV 8 Filter Pad (fabric, fiberglass, synthetic, etc.). Disposed along an inlet side 1005 of filter 1004 is an entrance support screen 1010. Disposed along an outlet side 1006 of filter 1004 is an inner separator screen 1020, an inner copper screen 1100, a separator screen 1030, and outer copper screen 1200, and an outer support screen 1040. The support screens and separator screens may be metallic, stainless steel screens.

In some embodiments, separator screen 1030 may be operable to randomize airflow coming out of inner copper screen 1100 made of a fabric, plastic, metallic foam, compressed wires, etc. The width of such a separator 1030 may be operable to adequately randomize the flow pattern of air passing through it, e.g., the width of such a separator 1030 may be twice the width of inner copper screen 1100. For example, in this embodiment, the separator between the two copper screens is made from a material which is operable to produce a randomized air flow pattern of the air exiting out of the first (inner) copper screen. This may ensure that even if the holes in the second (outer) copper screen are perfectly aligned with holes in the first (inner) copper screen (a very unlikely possibility), the air exiting out of the first (inner) copper screen may not go through straight out of the second (outer) copper screen.

Thus, if the copper screens are 400 mesh copper screens, such screens may have 38% open area and hence 62% of the incoming air particles will impact copper in the first screen allowing 38% to pass through without coming in contact with copper. The air coming out of this first (inner) copper screen will be randomized by the fabric separator between the two copper screens. Because the pattern of the air flow of the air coming out of the fabric separator is randomized, 62% of this air will impact the copper in the second (outer) copper screen. Hence, coronavirus particles exiting from the two copper screens will be 38%×38%=14.4% of the incoming air. Normal HVAC practice is to recirculate about 80% of the air with 20% fresh air. The amount of coronavirus coming out on a second pass through thus would be (14.4%× 20%+14.4%×14.4%×80%=) 4.6% of the concentration in the fresh air. The amount of coronavirus coming out on a third pass through thus would be (14.4%×20%+14.4%× 14.4%×14.4%×80%=) 3.2% of the concentration in the fresh air. After few passes the coronavirus level in the conditioned space would be 2.9% that of the level in the fresh incoming air. If a lower level is needed, the number of copper screens can be increased.

FIG. 12 illustrates a method 1300 for removing or deteriorating airborne contaminants from air, according to an embodiment of the present disclosure. In this illustrated embodiment, method 1300 may include, for example, at 1310 providing a copper wool medium configured to inactivate viruses from an air stream flowing therethrough, at 1320 assembling an elongate section onto each perimeter edge of the copper wool medium, at 1330 joining the elongate sections by way of corner sections section to create a rigid frame, at 1340 positioning the copper wool medium within a ventilation system, and at 1350 adjusting the rigid frame to direct the air stream to flow through the copper wool medium.

Method 1300 may further include the providing including selecting one or more copper or copper alloys that possess antimicrobial properties, and/or selecting a porosity that is less than or equal to 10 μm. The positioning may include orienting the copper wool medium such that the copper wool medium is downstream of a filter medium.

Testing was performed on a conventional air filer and an air filter according to the present disclosure suitable for use in an HVAC system of a commercial building.

Testing of a conventional pleated air filter (16 inch×25 inch×1 inch, PRE-PLEAT 40 LPD) was performed with measurement of the pressure drop across the conventional pleated air filter using a manometer made by Omega Inc. Part #HHC280. The observed pressure measurements included an upstream static air pressure of 0.60 inches of water and a downstream static air pressure of 0.30 inches of water, resulting in a pressure drop across the filter of 0.30 inches of water.

The conventional filter was replaced with a prototype air filter based on a modified conventional filter, according to the present disclosure. In this exemplary embodiment, the conventional filter was modified as follows: 1) The two outer layers of fabric in the conventional filter were left in place, and 2) the central fabric layer was replaced with a layer of copper wool from a one pound "fine grit" copper wool roll available from Rouge River Tool Company purchased through Amazon.com. The results of the pressure measurement included an upstream static air pressure of 0.54 inches of water and a downstream static air pressure 0.24 inches of water resulting in a pressure drop across the filter of 0.30 inches of water. The amount of copper in the prototype did not change the pressure drop in the two tests.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the present disclosure has been described in detail in connection with only a limited number of embodiments, it should be readily understood that the present disclosure is not limited to such disclosed embodiments. Rather, the invention can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the disclosure may include only some of the described embodiments.

Components, aspects, features, configurations, arrangements, uses and the like described, illustrated or otherwise disclosed herein with respect to any particular embodiment may be similarly applied to any other embodiment disclosed herein. Accordingly, the present disclosure is not to be seen as limited by the foregoing description, but is only limited by the scope of the appended claims.

This written description uses examples to disclose the present disclosure, including the best mode, and also to enable any person skilled in the art to practice the present disclosure, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An air filter to inactivate viruses, the air filter comprising:
    a first copper wool medium configured to inactivate viruses from an air stream flowing therethrough;
    a second copper wool medium configured to inactivate viruses from the air stream flowing therethrough;
    a non-copper metallic separator screen disposed between the first copper wool medium and the second copper wool medium configured to randomize the airflow coming out of the first copper wool medium and into the second copper wool medium rather than filter the airflow;
    a frame supporting the first copper wool medium, the separator screen, and the second copper wool medium; and
    wherein the degree of obstruction that the air filter imparts on the air stream flowing therethrough does not result in a significant increase in pressure drop.

2. The air filter of claim 1, wherein the copper wool medium has a porosity less than or equal to 10 μm.

3. The air filter of claim 1, wherein a pressure drop across the air filter due to the air stream is 0.30 inch of water.

4. The air filter of claim 1, wherein the frame is configured to be adjusted to accommodate an interior of a ventilation system.

5. The air filter of claim 1, wherein the copper wool medium is configured to inactivate coronaviruses from the air stream flowing therethrough.

6. The air filter of claim 1, wherein the copper wool medium comprises one or more copper or copper alloys with antimicrobial properties.

7. The air filter of claim 1, wherein the frame comprises a rigid material.

8. The air filter of claim 1, wherein the frame is configured to enable replacement of the first copper wool medium and the second copper wool medium.

9. The air filter of claim 1, wherein the first copper wool medium and the second copper wool medium comprise an upstream mesh screen and a downstream mesh screen, respectively.

10. A method for inactivating viruses, the method comprising:
    providing the air filter of claim 1; and
    recirculating in a closed loop a flow of the air stream through the air filter.

11. The air filter of claim 1, wherein the separator screen comprises a width twice the width of first copper wool medium.

12. The air filter of claim 1, further comprising:
    a first support screen disposed along an inlet side of the air filter such that the first copper wool medium is positioned between the first support screen and the separator screen; and
    a second support screen disposed along an outlet side of the air filter such that the second copper wool medium is positioned between the separator screen and the second support screen.

13. The air filter of claim 12, further comprising:
    an entrance support screen; and
    a particle filter disposed between the entrance support screen and the support screen disposed along the inlet side of the air filter.

14. The air filter of claim 12, wherein the support screens comprise metallic screens.

15. The air filter of claim 1, wherein:
    the first copper wool medium comprises a mesh copper screen; and
    the second copper wool medium comprises a mesh copper screen.

16. The air filter of claim 1, wherein:
    the first copper wool medium comprises a copper screen;
    the second copper wool medium comprises a copper screen; and
    wherein the air filter further comprises one or more additional copper screens.

17. The air filter of claim 1, wherein the air filter consists of a copper portion and a non-copper portion, the copper portion consisting of the first copper wool medium and the second copper wool medium.

18. The air filter of claim 1, wherein the air filter is configured such that airborne pathogens flow past the first copper wool medium and the second copper wool medium after contacting them.

19. The air filter of claim 1, wherein the first copper wool medium and the second copper wool medium are configured to allow inactivate airborne pathogens to flow there past after the pathogens contact the respective medium.

20. An air filter to inactivate viruses, the air filter comprising:
    a filter medium configured to inactivate viruses from an air stream flowing therethrough, the filter medium comprising:
        a first filter layer;
        an entrance support screen disposed adjacent to a first side of the first filter layer;
        an inner separator screen disposed adjacent to a second side of the first filter layer;

a first copper wool medium disposed adjacent to the inner separator screen;

a second copper wool medium;

a non-copper, non-filtering metallic separator screen disposed between the first copper wool medium and the second copper wool medium, said separator screen operable to randomize airflow coming out of the first copper wool medium and into the second copper wool medium; and a frame configured to support the filter medium.

21. The air filter of claim 20, wherein the first filter layer comprises a particulate filter.

22. The air filter of claim 20, wherein the first filter layer is a high-efficiency particulate air (HEPA) filter.

23. The air filter of claim 22, wherein the copper wool medium comprises a porosity less than or equal to 10 μm.

24. The air filter of claim 22, wherein the copper wool medium comprises one or more copper or copper alloys with antimicrobial properties.

25. The air filter of claim 20, wherein the frame comprises multiple elongated sections that are joined by corner sections and disposed along perimeter edges of the filter medium.

26. The air filter of claim 20, wherein:
the first filter layer comprises a particulate filter; and
the air filter further comprises an outlet support screen disposed adjacent to the second copper wool medium such that the second copper wool medium is positioned between the separator screen and the outlet support screen.

27. A method for inactivating viruses, the method comprising:
providing the air filtration system of claim 26; and
recirculating in a closed loop a flow of the air stream through the air filtration system.

28. An air filtration system comprising:
a first filter comprising copper configured to inactivate contaminants from an air stream flowing through a ventilation system;
a first frame configured to direct the air stream through the first filter;
a second filter comprising copper configured to inactivate contaminants from the air stream flowing through the ventilation system;
a channel extending between the first filter and the second filter such that the first filter and the second filter are in fluid communication; and
a non-copper metallic separator device positioned between the first and second filters configured to randomize the air stream flowing through the ventilation system between the first and second filters.

29. The air filtration system of claim 28, further comprising a second frame configured to direct the air stream through the second filter.

30. The air filtration system of claim 28, the channel further comprising:
a channel frame; and
a first ultraviolet light source affixed to an interior surface of the channel frame.

31. The air filtration system of claim 30, wherein the first filter is affixed to a first end of the channel frame and the second filter is affixed to a second end of the channel frame, wherein the first end is positioned opposite the second end.

32. The air filtration system of claim 31, wherein the first filter is positioned upstream of an air stream flowing through the ventilation system relative to the position of the second filter layer.

33. The air filtration system of claim 28, wherein the first and second filters comprise a copper filter medium that comprises one or more copper or copper alloys with antimicrobial properties.

34. The air filtration system of claim 33, wherein the copper filter medium comprises a porosity less than or equal to 10 μm.

35. A method for removing or deteriorating airborne contaminants from air, the method comprising:
providing and air filter comprising:
a first copper wool medium configured to inactivate viruses from an air stream flowing therethrough;
a second copper wool medium configured to inactivate viruses from the air stream flowing therethrough;
a non-copper metallic separator disposed between the first copper wool medium and the second copper wool medium configured to randomize the airflow coming out of the first copper wool medium and into the second copper wool medium;
assembling an elongate section onto each perimeter edge of the air filter, and joining the elongate sections by way of corner sections section to create a rigid frame;
positioning the air filter within the air stream of a ventilation system;
adjusting the rigid frame to direct the air stream to flow through the air filter; and
wherein the degree of obstruction that the air filter imparts on the air stream flowing therethrough does not result in a significant increase in pressure drop.

36. The method of claim 35, wherein the providing the copper wool medium comprises selecting one or more copper or copper alloys that possess antimicrobial properties.

37. The method of claim 35, wherein the providing the copper wool medium comprises selecting a porosity that is less than or equal to 10 μm.

38. The method of claim 35, wherein the positioning the copper wool medium comprises orienting the copper wool medium such that the copper wool medium is downstream of a filter medium.

* * * * *